United States Patent [19]
Garner et al.

[11] Patent Number: 5,905,185
[45] Date of Patent: May 18, 1999

[54] PROTEIN C PRODUCTION IN NON-HUMAN TRANSGENIC MAMMALS

[75] Inventors: Ian Garner; Ian R. Cottingham; Simon M. Temperley, all of Edinburgh, United Kingdom; Donald C. Foster, Seattle, Wash.; Cindy A. Sprecher, Seattle, Wash.; Donna E. Prunkard, Seattle, Wash.

[73] Assignees: PPL Therapeutics, Edinburgh, United Kingdom; ZymoGenetics, Inc., Seattle, Wash.

[21] Appl. No.: 08/756,506

[22] Filed: Nov. 26, 1996

Related U.S. Application Data

[60] Provisional application No. 60/019,692, Jun. 13, 1996, and provisional application No. 60/044,453, Nov. 30, 1995.

[51] Int. Cl.⁶ ............... A01K 67/027; C12P 21/00; C12P 21/06; C12N 15/00
[52] U.S. Cl. .................. 800/14; 800/4; 800/21; 435/69.1; 935/60
[58] Field of Search .............. 800/2; 435/69.1, 435/69.6, 212

[56] References Cited

U.S. PATENT DOCUMENTS

| | | | |
|---|---|---|---|
| 4,959,318 | 9/1990 | Foster et al. | 435/69.1 |
| 5,516,650 | 5/1996 | Foster et al. | 435/68.1 |
| 5,589,604 | 12/1996 | Drohan et al. | 800/2 |

FOREIGN PATENT DOCUMENTS

| | | |
|---|---|---|
| 319 312 | 6/1989 | European Pat. Off. . |
| 88/00239 | 1/1988 | WIPO . |
| 92/11757 | 7/1992 | WIPO . |
| 94/05796 | 3/1994 | WIPO . |

OTHER PUBLICATIONS

Colman et al., *Miami Bio/Technology Short Reports* (6): 107,1995.
Foster et al., *Biochemistry* 29: 347–354, 1990.
Drohan et al., *Transgenic Research* 3: 355–364, 1994.
Foster et al., *Proc. Natl. Acad. Sci. U.S.A.* 82: 4673–4677, 1985.
Drews et al., *Proc. Natl. Acad. Sci. U.S.A.* 92: 10462–10466, 1995.
Busby et al., *Current Advances in Vitamin K Research*: 173–181, 1987.
Foster et al., *Biochemistry* 26: 7003–7011, 1987.
Velander et al., *Proc. Natl. Acad. Sci. U.S.A.* 89: 12003–12007, 1992.
Velander et al., *Annals New York Academy of Sciences*: 391–403, 1992.

*Primary Examiner*—Deborah Crouch
*Attorney, Agent, or Firm*—Deborah A. Sawislak

[57] ABSTRACT

Methods for producing protein C in transgenic non-human mammals are disclosed. The protein C is modified at the two-chain cleavage site between the light and heavy chains of protein C from Lys-Arg to $R_1$-$R_2$-$R_3$-$R_4$ where $R_1$ through $R_4$ are individually Arg or Lys. DNA segments encoding modified protein C are introduced into the germ line of a non-human mammals, and the mammal or its female progeny produces milk containing protein C expressed from the introduced DNA segments. The protein C expressed from the introduced DNA segments has anticoagulant activity when activated. Non-human mammalian embryos and transgenic non-human mammals carrying DNA segments encoding heterologous protein C are also disclosed.

17 Claims, 5 Drawing Sheets

SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
        (A) LENGTH: 11725 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: join(3520..3630, 5093..5117, 5210..5347, 5450
            ..5584, 8253..8395, 9269..9386, 10516..11102)

(xi) SEQUENCE DESCRIPTION: SEQ ID NO:1:

```
AGTGAATCTG GGCGAGTAAC ACAAAACTTG AGTGTCCTTA CCTGAAAAAT AGAGGTTAGA      60

GGGATGCTAT GTGCCATTGT GTGTGTGTGT TGGGGGTGGG GATTGGGGGT GATTTGTGAG     120

CAATTGGAGG TGAGGGTGGA GCCCAGTGCC CAGCACCTAT GCACTGGGGA CCCAAAAAGG     180

AGCATCTTCT CATGATTTTA TGTATCAGAA ATTGGGATGG CATGTCATTG GGACAGCGTC     240

TTTTTTCTTG TATGGTGGCA CATAAATACA TGTGTCTTAT AATTAATGGT ATTTTAGATT     300

TGACGAAATA TGGAATATTA CCTGTTGTGC TGATCTTGGG CAAACTATAA TATCTCTGGG     360

CAAAAATGTC CCCATCTGAA AAACAGGGAC AACGTTCCTC CCTCAGCCAG CCACTATGGG     420

GCTAAAATGA GACCACATCT GTCAAGGGTT TTGCCCTCAC CTCCCTCCCT GCTGGATGGC     480

ATCCTTGGTA GGCAGAGGTG GGCTTCGGGC AGAACAAGCC GTGCTGAGCT AGGACCAGGA     540

GTGCTAGTGC CACTGTTTGT CTATGGAGAG GGAGGCCTCA GTGCTGAGGG CCAAGCAAAT     600

ATTTGTGGTT ATGGATTAAC TCGAACTCCA GGCTGTCATG GCGGCAGGAC GGCGAACTTG     660

CAGTATCTCC ACGACCCGCC CCTGTGAGTC CCCCTCCAGG CAGGTCTATG AGGGGTGTGG     720

AGGGAGGGCT GCCCCCGGGA GAAGAGAGCT AGGTGGTGAT GAGGGCTGAA TCCTCCAGCC     780

AGGGTGCTCA ACAAGCCTGA GCTTGGGGTA AAAGGACACA AGGCCCTCCA CAGGCCAGGC     840

CTGGCAGCCA CAGTCTCAGG TCCCTTTGCC ATGCGCCTCC CTCTTTCCAG GCCAAGGGTC     900

CCCAGGCCCA GGGCCATTCC AACAGACAGT TTGGAGCCCA GGACCCTCCA TTCTCCCCAC     960

CCCACTTCCA CCTTTGGGGG TGTCGGATTT GAACAAATCT CAGAAGCGGC CTCAGAGGGA    1020

GTCGGCAAGA ATGGAGAGCA GGGTCCGGTA GGGTGTGCAG AGGCCACGTG GCCTATCCAC    1080

TGGGGAGGGT TCCTTGATCT CTGGCCACCA GGGCTATCTC TGTGGCCTTT TGGAGCAACC    1140

TGGTGGTTTG GGGCAGGGGT TGAATTTCCA GGCCTAAAAC CACACAGGCC TGGCCTTGAG    1200
```

```
TCCTGGCTCT GCGAGTAATG CATGGATGTA AACATGGAGA CCCAGGACCT TGCCTCAGTC      1260

TTCCGAGTCT GGTGCCTGCA GTGTACTGAT GGTGTGAGAC CCTACTCCTG GAGGATGGGG      1320

GACAGAATCT GATCGATCCC CTGGGTTGGT GACTTCCCTG TGCAATCAAC GGAGACCAGC      1380

AAGGGTTGGA TTTTTAATAA ACCACTTAAC TCCTCCGAGT CTCAGTTTCC CCCTCTATGA      1440

AATGGGGTTG ACAGCATTAA TAACTACCTC TTGGGTGGTT GTGAGCCTTA ACTGAAGTCA      1500

TAATATCTCA TGTTTACTGA GCATGAGCTA TGTGCAAAGC CTGTTTTGAG AGCTTTATGT      1560

GGACTAACTC CTTTAATTCT CACAACACCC TTTAAGGCAC AGATACACCA CGTTATTCCA      1620

TCCATTTTAC AAATGAGGAA ACTGAGGCAT GGAGCAGTTA AGCATCTTGC CCAACATTGC      1680

CCTCCAGTAA GTGCTGGAGC TGGAATTTGC ACCGTGCAGT CTGGCTTCAT GGCCTGCCCT      1740

GTGAATCCTG TAAAAATTGT TTGAAAGACA CCATGAGTGT CCAATCAACG TTAGCTAATA      1800

TTCTCAGCCC AGTCATCAGA CCGGCAGAGG CAGCCACCCC ACTGTCCCCA GGAGGACAC      1860

AAACATCCTG GCACCCTCTC CACTGCATTC TGGAGCTGCT TTCTAGGCAG GCAGTGTGAG      1920

CTCAGCCCCA CGTAGAGCGG GCAGCCGAGG CCTTCTGAGG CTATGTCTCT AGCGAACAAG      1980

GACCCTCAAT TCCAGCTTCC GCCTGACGGC CAGCACACAG GGACAGCCCT TTCATTCCGC      2040

TTCCACCTGG GGGTGCAGGC AGAGCAGCAG CGGGGGTAGC ACTGCCCGGA GCTCAGAAGT      2100

CCTCCTCAGA CAGGTGCCAG TGCCTCCAGA ATGTGGCAGC TCACAAGCCT CCTGCTGTTC      2160

GTGGCCACCT GGGGAATTTC CGGCACACCA GCTCCTCTTG GTAAGGCCAC CCCACCCCTA      2220

CCCCGGGACC CTTGTGGCCT CTACAAGGCC CTGGTGGCAT CTGCCCAGGC CTTCACAGCT      2280

TCCACCATCT CTCTGAGCCC TGGGTGAGGT GAGGGGCAGA TGGGAATGGC AGGAATCAAC      2340

TGACAAGTCC CAGGTAGGCC AGCTGCCAGA GTGCCACACA GGGGCTGCCA GGGCAGGCAT      2400

GCGTGATGGC AGGGAGCCCC GCGATGACCT CCTAAAGCTC CCTCCTCCAC ACGGGGATGG      2460

TCACAGAGTC CCCTGGGCCT TCCCTCTCCA CCCACTCACT CCCTCAACTG TGAAGACCCC      2520

AGGCCCAGGC TACCGTCCAC ACTATCCAGC ACAGCCTCCC CTACTCAAAT GCACACTGGC      2580

CTCATGGCTG CCCTGCCCCA ACCCCTTTCC TGGTCTCCAC AGCCAACGGG AGGAGGCCAT      2640

GATTCTTGGG GAGGTCCGCA GGCACATGGG CCCCTAAAGC CACACCAGGC TGTTGGTTTC      2700

ATTTGTGCCT TTATAGAGCT GTTTATCTGC TTGGACCTG CACCTCCACC CTTTCCCAAG      2760

GTGCCCTCAG CTCAGGCATA CCCTCCTCTA GGATGCCTTT TCCCCCATCC CTTCTTGCTC      2820

ACACCCCAA CTTGATCTCT CCCTCCTAAC TGTGCCCTGC ACCAAGACAG ACACTTCACA      2880

GAGCCCAGGA CACACCTGGG GACCCTTCCT GGGTGATAGG TCTGTCTATC CTCCAGGTGT      2940

CCCTGCCCAA GGGGAGAAGC ATGGGGAATA CTTGGTTGGG GGAGGAAAGG AAGACTGGGG      3000

GGATGTGTCA AGATGGGGCT GCATGTGGTG TACTGGCAGA AGAGTGAGAG GATTTAACTT      3060

GGCAGCCTTT ACAGCAGCAG CCAGGGCTTG AGTACTTATC TCTGGGCCAG GCTGTATTGG      3120

ATGTTTTACA TGACGGTCTC ATCCCCATGT TTTTGGATGA GTAAATTGAA CCTTAGAAAG      3180

GTAAAGACAC TGGCTCAAGG TCACACAGAG ATCGGGTGG GGTTCACAGG GAGGCCTGTC      3240

CATCTCAGAG CAAGGCTTCG TCCTCCAACT GCCATCTGCT TCCTGGGGAG GAAAAGAGCA      3300

GAGGACCCCT GCGCCAAGCC ATGACCTAGA ATTAGAATGA GTCTTGAGGG GGCGGAGACA      3360

AGACCTTCCC AGGCTCTCCC AGCTCTGCTT CCTCAGACCC CCTCATGGCC CCAGCCCCTC      3420

TTAGGCCCCT CACCAAGGTG AGCTCCCCTC CCTCCAAAAC CAGACTCAGT GTTCTCCAGC      3480

AGCGAGCGTG CCCACCAGGT GCTGCGGATC CGCAAACGT GCC AAC TCC TTC CTG          3534

GAG GAG CTC CGT CAC AGC AGC CTG GAG CGG GAG TGC ATA GAG GAG ATC        3582
```

-continued

```
TGT GAC TTC GAG GAG GCC AAG GAA ATT TTC CAA AAT GTG GAT GAC ACA        3630

GTAAGGCCAC CATGGGTCCA GAGGATGAGG CTCAGGGGCG AGCTGGTAAC CAGCAGGGGC      3690

CTCGAGGAGC AGGTGGGGAC TCAATGCTGA GGCCCTCTTA GGAGTTGTGG GGGTGGCTGA      3750

GTGGAGCGAT TAGGATGCTG GCCCTATGAT GTCGGCCAGG CACATGTGAC TGCAAGAAAC      3810

AGAATTCAGG AAGAAGCTCC AGGAAAGAGT GTGGGGTGAC CCTAGGTGGG GACTCCCACA      3870

GCCACAGTGT AGGTGGTTCA GTCCACCCTC CAGCCACTGC TGAGCACCAC TGCCTCCCCG      3930

TCCCACCTCA CAAAGAGGGG ACCTAAAGAC CACCCTGCTT CCACCCATGC CTCTGCTGAT      3990

CAGGGTGTGT GTGTGACCGA AACTCACTTC TGTCCACATA AAATCGCTCA CTCTGTGCCT      4050

CACATCAAAG GGAGAAAATC TGATTGTTCA GGGGTCGGA AGACAGGGTC TGTGTCCTAT       4110

TTGTCTAAGG GTCAGAGTCC TTTGGAGCCC CCAGAGTCCT GTGGACGTGG CCCTAGGTAG      4170

TAGGGTGAGC TTGGTAACGG GGCTGGCTTC CTGAGACAAG GCTCAGACCC GCTCTGTCCC      4230

TGGGGATCGC TTCAGCCACC AGGACCTGAA AATTGTGCAC GCCTGGGCCC CCTTCCAAGG      4290

CATCCAGGGA TGCTTTCCAG TGGAGGCTTT CAGGGCAGGA GACCCTCTGG CCTGCACCCT      4350

CTCTTGCCCT CAGCCTCCAC CTCCTTGACT GGACCCCCAT CTGGACCTCC ATCCCCACCA      4410

CCTCTTTCCC CAGTGGCCTC CCTGGCAGAC ACCACAGTGA CTTTCTGCAG GCACATATCT     4470

GATCACATCA AGTCCCCACC GTGCTCCCAC CTCACCCATG GTCTCTCAGC CCCAGCAGCC      4530

TTGGCTGGCC TCTCTGATGG AGCAGGCATC AGGCACAGGC CGTGGGTCTC AACGTGGGCT      4590

GGGTGGTCCT GGACCAGCAG CAGCCGCCGC AGCAGCAACC CTGGTACCTG GTTAGGAACG     4650

CAGACCCTCT GCCCCCATCC TCCCAACTCT GAAAAACACT GGCTTAGGGA AAGGCGCGAT      4710

GCTCAGGGGT CCCCCAAAGC CCGCAGGCAG AGGGAGTGAT GGGACTGGAA GGAGGCCGAG      4770

TGACTTGGTG AGGGATTCGG GTCCCTTGCA TGCAGAGGCT GCTGTGGGAG CGGACAGTCG      4830

CGAGAGCAGC ACTGCAGCTG CATGGGGAGA GGGTGTTGCT CCAGGGACGT GGGATGGAGG     4890

CTGGGCGCGG GCGGGTGGCG CTGGAGGGCG GGGGAGGGGC AGGGAGCACC AGCTCCTAGC     4950

AGCCAACGAC CATCGGGCGT CGATCCCTGT TTGTCTGGAA GCCCTCCCCT CCCCTGCCCG      5010

CTCACCCGCT GCCCTGCCCC ACCCGGGCGC GCCCCTCCGC ACACCGGCTG CAGGAGCCTG     5070

ACGCTGCCCG CTCTCTCCGC AG CTG GCC TTC TGG TCC AAG CAC GTC  G           5117

GTGAGTGCGT TCTAGATCCC CGGCTGGACT ACCGGCGCCC GCGCCCCTCG GGATCTCTGG     5177

CCGCTGACCC CCTACCCCGC CTTGTGTCGC AG  AC GGT GAC CAG TGC TTG GTC      5229

TTG CCC TTG GAG CAC CCG TGC GCC AGC CTG TGC TGC GGG CAC GGC ACG      5277
TGC ATC GAC GGC ATC GGC AGC TTC AGC TGC GAC TGC CGC AGC GGC TGG      5325
GAG GGC CGC TTC TGC CAG CGC  G GTGAGGGGA GAGGTGGATG CTGGCGGGCG        5377
GCGGGCGGG GCTGGGGCCG GGTTGGGGGC GCGGCACCAG CACCAGCTGC CCGCGCCCTC      5437

CCCTGCCCGC AG  AG GTG AGC TTC CTC AAT TGC TCT CTG GAC AAC GGC         5484

GGC TGC ACG CAT TAC TGC CTA GAG GAG GTG GGC TGG CGG CGC TGT AGC      5532

TGT GCG CCT GGC TAC AAG CTG GGG GAC GAC CTC CTG CAG TGT CAC CCC      5580

GCA  G GTGAGAAGCC CCCAATACAT CGCCCAGGAA TCACGCTGGG TGCGGGGTGG         5634

GCAGGCCCCT GACGGGCGCG CGCGCGGGGG CTCAGGAGGG TTTCTAGGGA GGGAGCGAGG     5694

AACAGAGTTG AGCCTTGGGG CAGCGGCAGA CGCGCCCAAC ACCGGGGCCA CTGTTAGCGC     5754

AATCAGCCCG GGAGCTGGGC GCGCCCTCCG CTTTCCCTGC TTCCTTTCTT CCTGGCGTCC     5814

CCGCTTCCTC CGGGCGCCCC TGCGACCTGG GGCCACCTCC TGGAGCGCAA GCCCAGTGGT     5874

GGCTCCGCTC CCCAGTCTGA GCGTATCTGG GGCGAGGCGT GCAGCGTCCT CCTCCATGTA     5934
```

```
GCCTGGCTGC GTTTTTCTCT GACGTTGTCC GGCGTGCATC GCATTTCCCT CTTTACCCCC    5994

TTGCTTCCTT GAGGAGAGAA CAGAATCCCG ATTCTGCCTT CTTCTATATT TTCCTTTTTA    6054

TGCATTTTAA TCAAATTTAT ATATGTATGA AACTTTAAAA ATCAGAGTTT TACAACTCTT    6114

ACACTTTCAG CATGCTGTTC CTTGGCATGG GTCCTTTTTT CATTCATTTT CATAAAAGGT    6174

GGACCCTTTT AATGTGGAAA TTCCTATCTT CTGCCTCTAG GGCATTTATC ACTTATTTCT    6234

TCTACAATCT CCCCTTTACT TCCTCTATTT TCTCTTTCTG GACCTCCCAT TATTCAGACC    6294

TCTTTCCTCT AGTTTTATTG TCTCTTCTAT TTCCCATCTC TTTGACTTTG TGTTTTCTTT    6354

CAGGGAACTT TCTTTTTTTT CTTTTTTTTT GAGATGGAGT TTCACTCTTG TTGTCCCAGG    6414

CTGGAGTGCA ATGACGTGAT CTCAGCTCAC CACAACCTCC GCCTCCTGGA TTCAAGCGAT    6474

TCTCCTGCCG CAGCCTCCCG AGTAGCTGGG ATTACAGGCA TGCGCCACCA CGCCCAGCTA    6534

ATTTTGTGTT TTTAGTAGAG AAGGGGTTTC TCCGTGTTGG TCAAGCTGGT CTTGAACTCC    6594

TGACCTCAGG TGATCCACCT GCCTTGGCCT CCTAAAGTGC TGGGATTACA GGCGTGAGCC    6654

ACCGCGCCCA GCCTCTTTCA GGAACTTTC TACAACTTTA TAATTCAATT CTTCTGCAGA    6714

AAAAAATTTT TGGCCAGGCT CAGTAGCTCA GACCAATAAT TCCAGCACTT TGAGAGGCTG    6774

AGGTGGGAGG ATTGCTTGAG CTTGGGAGTT TGAGACTAGC CTGGGCAACA CAGTGAGACC    6834

CTGTCTCTAT TTTTAAAAAA AGTAAAAAAA GATCTAAAAA TTTAACTTTT TATTTTGAAA    6894

TAATTAGATA TTTCCAGGAA GCTGCAAAGA AATGCCTGGT GGGCCTGTTG GCTGTGGGTT    6954

TCCTGCAAGG CCGTGGGAAG GCCCTGTCAT TGGCAGAACC CCAGATCGTG AGGGCTTTCC    7014

TTTTAGGCTG CTTTCTAAGA GGACTCCTCC AAGCTCTTGG AGGATGGAAG ACGCTCACCC    7074

ATGGTGTTCG GCCCCTCAGA GCAGGGTGGG GCAGGGGAGC TGGTGCCTGT GCAGGCTGTG    7134

GACATTTGCA TGACTCCCTG TGGTCAGCTA AGAGCACCAC TCCTTCCTGA AGCGGGGCCT    7194

GAAGTCCCTA GTCAGAGCCT CTGGTTCACC TTCTGCAGGC AGGGAGAGGG GAGTCAAGTC    7254

AGTGAGGAGG GCTTTCGCAG TTTCTCTTAC AAACTCTCAA CATGCCCTCC CACCTGCACT    7314

GCCTTCCTGG AAGCCCCACA GCCTCCTATG GTTCCGTGGT CCAGTCCTTC AGCTTCTGGG    7374

CGCCCCCATC ACGGGCTGAG ATTTTTGCTT TCCAGTCTGC CAAGTCAGTT ACTGTGTCCA    7434

TCCATCTGCT GTCAGCTTCT GGAATTGTTG CTGTTGTGCC CTTTCCATTC TTTTGTTATG    7494

ATGCAGCTCC CCTGCTGACG ACGTCCCATT GCTCTTTTAA GTCTAGATAT CTGGACTGGG    7554

CATTCAAGGC CCATTTTGAG CAGAGTCGGG CTGACCTTTC AGCCCTCAGT TCTCCATGGA    7614

GTATGCGCTC TCTTCTTGGC AGGGAGGCCT CACAAACATG CCATGCCTAT TGTAGCAGCT    7674

CTCCAAGAAT GCTCACCTCC TTCTCCCTGT AATTCCTTTC CTCTGTGAGG AGCTCAGCAG    7734

CATCCCATTA TGAGACCTTA CTAATCCCAG GGATCACCCC CAACAGCCCT GGGGTACAAT    7794

GAGCTTTTAA GAAGTTTAAC CACCTATGTA AGGAGACACA GGCAGTGGGC GATGCTGCCT    7854

GGCCTGACTC TTGCCATTGG GTGGTACTGT TTGTTGACTG ACTGACTGAC TGACTGGAGG    7914

GGGTTTGTAA TTTGTATCTC AGGGATTACC CCCAACAGCC CTGGGGTACA ATGAGCCTTC    7974

AAGAAGTTTA ACAACCTATG TAAGGACACA CAGCCAGTGG GTGATGCTGC CTGGTCTGAC    8034

TCTTGCCATT CAGTGGCACT GTTTGTTGAC TGACTGACTG ACTGACTGGC TGACTGGAGG    8094

GGGTTCATAG CTAATATTAA TGGAGTGGTC TAAGTATCAT TGGTTCCTTG AACCCTGCAC    8154

TGTGGCAAAG TGGCCCACAG GCTGGAGGAG GACCAAGACA GGAGGGCAGT CTCGGGAGGA    8214

GTGCCTGGCA GGCCCCTCAC CACCTCTGCC TACCTCAG TG AAG TTC CCT TGT        8266

GGG AGG CCC TGG AAG CGG ATG GAG AAG AAG CGC AGT CAC CTG AAA CGA    8314
```

```
GAC ACA GAA GAC CAA GAA GAC CAA GTA GAT CCG CGG CTC ATT GAT GGG      8362

AAG ATG ACC AGG CGG GGA GAC AGC CCC TGG CAG GTGGGAGGCG AGGCAGCACC    8415

GGCTCGTCAC GTGCTGGGTC CGGGATCACT GAGTCCATCC TGGCAGCTAT GCTCAGGGTG    8475

CAGAAACCGA GAGGGAAGCG CTGCCATTGC GTTTGGGGGA TGATGAAGGT GGGGGATGCT    8535

TCAGGGAAAG ATGGACGCAA CCTGAGGGGA GAGGAGCAGC CAGGGTGGGT GAGGGGAGGG    8595

GCATGGGGGC ATGGAGGGGT CTGCAGGAGG GAGGGTTACA GTTTCTAAAA AGAGCTGGAA    8655

AGACACTGCT CTGCTGGCGG GATTTTAGGC AGAAGCCCTG CTGATGGGAG AGGGCTAGGA    8715

GGGAGGGCCG GGCCTGAGTA CCCCTCCAGC CTCCACATGG GAACTGACAC TTACTGGGTT    8775

CCCCTCTCTG CCAGGCATGG GGGAGATAGG AACCAACAAG TGGGAGTATT TGCCCTGGGG    8835

ACTCAGACTC TGCAAGGGTC AGGACCCCAA AGACCCGGCA GCCCAGTGGG ACCACAGCCA    8895

GGACGGCCCT TCAAGATAGG GGCTGAGGGA GGCCAAGGGG AACATCCAGG CAGCCTGGGG    8955

GCCACAAAGT CTTCCTGGAA GACACAAGGC CTGCCAAGCC TCTAAGGATG AGAGGAGCTC    9015

GCTGGGCGAT GTTGGTGTGG CTGAGGGTGA CTGAAACAGT ATGAACAGTG CAGGAACAGC    9075

ATGGGCAAAG GCAGGAAGAC ACCCTGGGAC AGGCTGACAC TGTAAAATGG GCAAAAATAG    9135

AAAACGCCAG AAAGGCCTAA GCCTATGCCC ATATGACCAG GGAACCCAGG AAAGTGCATA    9195

TGAAACCCAG GTGCCCTGGA CTGGAGGCTG TCAGGAGGCA GCCCTGTGAT GTCATCATCC    9255

CACCCCATTC CAG GTG GTC CTG CTG GAC TCA AAG AAG AAG CTG GCC TGC       9304

GGG GCA GTG CTC ATC CAC CCC TCC TGG GTG CTG ACA GCG GCC CAC TGC     9352

ATG GAT GAG TCC AAG AAG CTC CTT GTC AGG CTT  G GTATGGGCTG            9396

GAGCCAGGCA GAAGGGGGCT GCCAGAGGCC TGGGTAGGGG GACCAGGCAG GCTGTTCAGG    9456

TTTGGGGGAC CCCGCTCCCC AGGTGCTTAA GCAAGAGGCT TCTTGAGCTC CACAGAAGGT    9516

GTTTGGGGGG AAGAGGCCTA TGTGCCCCCA CCCTGCCCAC CCATGTACAC CCAGTATTTT    9576

GCAGTAGGGG GTTCTCTGGT GCCCTCTTCG AATCTGGGCA CAGGTACCTG CACACACATG    9636

TTTGTGAGGG GCTACACAGA CCTTCACCTC TCCACTCCCA CTCATGAGGA GCAGGCTGTG    9696

TGGGCCTCAG CACCCTTGGG TGCAGAGACC AGCAAGGCCT GGCCTCAGGG CTGTGCCTCC    9756

CACAGACTGA CAGGGATGGA GCTGTACAGA GGGAGCCCTA GCATCTGCCA AAGCCACAAG    9816

CTGCTTCCCT AGCAGGCTGG GGGCTCCTAT GCATTGGCCC CGATCTATGG CAATTTCTGG    9876

AGGGGGGTC TGGCTCAACT CTTTATGCCA AAAAGAAGGC AAAGCATATT GAGAAAGGCC     9936

AAATTCACAT TTCCTACAGC ATAATCTATG CCAGTGGCCC CGTGGGGCTT GGCTTAGAAT    9996

TCCCAGGTGC TCTTCCCAGG GAACCATCAG TCTGGACTGA GAGGACCTTC TCTCTCAGGT    10056

GGGACCCGGC CCTGTCCTCC CTGGCAGTGC CGTGTTCTGG GGGTCCTCCT CTCTGGGTCT    10116

CACTGCCCCT GGGGTCTCTC CAGCTACCTT TGCTCCATGT TCCTTTGTGG CTCTGGTCTG    10176

TGTCTGGGGT TTCCAGGGGT CTCGGGCTTC CCTGCTGCCC ATTCCTTCTC TGGTCTCACG    10236

GCTCCGTGAC TCCTGAAAAC CAACCAGCAT CCTACCCCTT TGGATTGACA CCTGTTGGCC    10296

ACTCCTTCTG GCAGGAAAAG TCACCGTTGA TAGGGTTCCA CGGCATAGAC AGGTGGCTCC    10356

GCGCCAGTGC CTGGGACGTG TGGGTGCACA GTCTCCGGGT GAACCTTCTT CAGGCCCTCT    10416

CCCAGGCCTG CAGGGGCACA GCAGTGGGTG GGCCTCAGGA AAGTGCCACT GGGGAGAGGC    10476

TCCCCGCAGC CCACTCTGAC TGTGCCCTCT GCCCTGCAG  GA GAG TAT GAC CTG      10529

CGG CGC TGG GAG AAG TGG GAG CTG GAC CTG GAC ATC AAG GAG GTC TTC    10577

GTC CAC CCC AAC TAC AGC AAG AGC ACC ACC GAC AAT GAC ATC GCA CTG    10625
```

-continued

```
CTG CAC CTG GCC CAG CCC GCC ACC CTC TCG CAG ACC ATA GTG CCC ATC    10673

TGC CTC CCG GAC AGC GGC CTT GCA GAG CGC GAG CTC AAT CAG GCC GGC    10721

CAG GAG ACC CTC GTG ACG GGC TGG GGC TAC CAC AGC AGC CGA GAG AAG    10769

GAG GCC AAG AGA AAC CGC ACC TTC GTC CTC AAC TTC ATC AAG ATT CCC    10817

GTG GTC CCG CAC AAT GAG TGC AGC GAG GTC ATG AGC AAC ATG GTG TCT    10865

GAG AAC ATG CTG TGT GCG GGC ATC CTC GGG GAC CGG CAG GAT GCC TGC    10913

GAG GGC GAC AGT GGG GGG CCC ATG GTC GCC TCC TTC CAC GGC ACC TGG    10961

TTC CTG GTG GGC CTG GTG AGC TGG GGT GAG GGC TGT GGG CTC CTT CAC    11009

AAC TAC GGC GTT TAC ACC AAA GTC AGC CGC TAC CTC GAC TGG ATC CAT    11057

GGG CAC ATC AGA GAC AAG GAA GCC CCC CAG AAG AGC TGG GCA CCT        11102

TAGCGACCCT CCCTGCAGGG CTGGGCTTTT GCATGGCAAT GGATGGGACA TTAAAGGGAC  11162

ATGTAACAAG CACACCGGCC TGCTGTTCTG TCCTTCCATC CCTCTTTTGG GCTCTTCTGG  11222

AGGGAAGTAA CATTTACTGA GCACCTGTTG TATGTCACAT GCCTTATGAA TAGAATCTTA  11282

ACTCCTAGAG CAACTCTGTG GGGTGGGGAG GAGCAGATCC AAGTTTTGCG GGTCTAAAG   11342

CTGTGTGTGT TGAGGGGGAT ACTCTGTTTA TGAAAAAGAA TAAAAAACAC AACCACGAAG  11402

CCACTAGAGC CTTTTCCAGG GCTTTGGGAA GAGCCTGTGC AAGCCGGGGA TGCTGAAGGT  11462

GAGGCTTGAC CAGCTTTCCA GCTAGCCCAG CTATGAGGTA GACATGTTTA GCTCATATCA  11522

CAGAGGAGGA AACTGAGGGG TCTGAAAGGT TTACATGGTG GAGCCAGGAT TCAAATCTAG  11582

GTCTGACTCC AAAACCCAGG TGCTTTTTTC TGTTCTCCAC TGTCCTGGAG ACAGCTGTT   11642

TCGACGGTGC TCAGTGTGGA GGCCACTATT AGCTCTGTAG GGAAGCAGCC AGAGACCCAG  11702

AAAGTGTTGG TTCAGCCCAG AAT                                         11725
```

(2) INFORMATION FOR SEQ ID NO:2:

(i) SEQUENCE CHARACTERISTICS:
        (A) LENGTH: 460 amino acids
        (B) TYPE: amino acid
        (D) TOPOLOGY: linear (ii) MOLECULE TYPE: protein (xi) SEQUENCE DESCRIPTION: SEQ ID NO:2:

```
Met Trp Gln Leu Thr Ser Leu Leu Phe Val Ala Thr Trp Gly Ile
 1               5                  10                  15

Ser Gly Thr Pro Ala Pro Leu Asp Ser Val Phe Ser Ser Glu Arg
                20                  25                  30

Ala His Gln Val Leu Arg Ile Arg Lys Arg Ala Asn Ser Phe Leu Glu
                35                  40                  45

Glu Leu Arg His Ser Ser Leu Glu Arg Glu Cys Ile Glu Glu Ile Cys
 50                  55                  60

Asp Phe Glu Glu Ala Lys Glu Ile Phe Gln Asn Val Asp Asp Thr Leu
 65                  70                  75                  80

Ala Phe Trp Ser Lys His Val Asp Gly Asp Gln Cys Leu Val Leu Pro
                85                  90                  95

Leu Glu His Pro Cys Ala Ser Leu Cys Cys Gly His Gly Thr Cys Ile
                100                 105                 110

Asp Gly Ile Gly Ser Phe Ser Cys Asp Cys Arg Ser Gly Trp Glu Gly
                115                 120                 125

Arg Phe Cys Gln Arg Glu Val Ser Phe Leu Asn Cys Ser Leu Asp Asn
130                 135                 140
```

```
Gly Gly Cys Thr His Tyr Cys Leu Glu Val Gly Trp Arg Arg Cys
145                 150                 155                 160

Ser Cys Ala Pro Gly Tyr Lys Leu Gly Asp Asp Leu Leu Gln Cys His
                165                 170                 175

Pro Ala Val Lys Phe Pro Cys Gly Arg Pro Trp Lys Arg Met Glu Lys
            180                 185                 190

Lys Arg Ser His Leu Lys Arg Asp Thr Glu Asp Gln Glu Asp Gln Val
        195                 200                 205

Asp Pro Arg Leu Ile Asp Gly Lys Met Thr Arg Arg Gly Asp Ser Pro
    210                 215                 220

Trp Gln Val Val Leu Leu Asp Ser Lys Lys Lys Leu Ala Cys Gly Ala
225                 230                 235                 240

Val Leu Ile His Pro Ser Trp Val Leu Thr Ala Ala His Cys Met Asp
                245                 250                 255

Glu Ser Lys Lys Leu Leu Val Arg Leu Gly Glu Tyr Asp Leu Arg Arg
            260                 265                 270

Trp Glu Lys Trp Glu Leu Asp Leu Asp Ile Lys Glu Val Phe Val His
        275                 280                 285

Pro Asn Tyr Ser Lys Ser Thr Thr Asp Asn Asp Ile Ala Leu Leu His
    290                 295                 300

Leu Ala Gln Pro Ala Thr Leu Ser Gln Thr Ile Val Pro Ile Cys Leu
305                 310                 315                 320

Pro Asp Ser Gly Leu Ala Glu Arg Glu Leu Asn Gln Ala Gly Gln Glu
                325                 330                 335

Thr Leu Val Thr Gly Trp Gly Tyr His Ser Ser Arg Glu Lys Glu Ala
            340                 345                 350

Lys Arg Asn Arg Thr Phe Val Leu Asn Phe Ile Lys Ile Pro Val Val
        355                 360                 365

Pro His Asn Glu Cys Ser Glu Val Met Ser Asn Met Val Ser Glu Asn
    370                 375                 380

Met Leu Cys Ala Gly Ile Leu Gly Asp Arg Gln Asp Ala Cys Glu Gly
385                 390                 395                 400

Asp Ser Gly Gly Pro Met Val Ala Ser Phe His Gly Thr Trp Phe Leu
                405                 410                 415

Val Gly Leu Val Ser Trp Gly Glu Gly Cys Gly Leu Leu His Asn Tyr
            420                 425                 430

Gly Val Tyr Thr Lys Val Ser Arg Tyr Leu Asp Trp Ile His Gly His
        435                 440                 445

Ile Arg Asp Lys Glu Ala Pro Gln Lys Ser Trp Ala
450                 455                 460

(2) INFORMATION FOR SEQ ID NO:3:

(i) SEQUENCE CHARACTERISTICS:
        (A) LENGTH: 1386 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..1380

(xi) SEQUENCE DESCRIPTION: SEQ ID NO:3:

ATG TGG CAG CTC ACA AGC CTC CTG CTG TTC GTG GCC ACC TGG GGA ATT      48
Met Trp Gln Leu Thr Ser Leu Leu Leu Phe Val Ala Thr Trp Gly Ile
```

```
            1                   5                    10                   15
TCC GGC ACA CCA GCT CCT CTT GAC TCA GTG TTC TCC AGC AGC GAG CGT        96
Ser Gly Thr Pro Ala Pro Leu Asp Ser Val Phe Ser Ser Ser Glu Arg
             20                  25                  30

GCC CAC CAG GTG CTG CGG ATC CGC AAA CGT GCC AAC TCC TTC CTG GAG       144
Ala His Gln Val Leu Arg Ile Arg Lys Arg Ala Asn Ser Phe Leu Glu
             35                  40                  45

GAG CTC CGT CAC AGC AGC CTG GAG CGG GAG TGC ATA GAG GAG ATC TGT       192
Glu Leu Arg His Ser Ser Leu Glu Arg Glu Cys Ile Glu Glu Ile Cys
         50                  55                  60

GAC TTC GAG GAG GCC AAG GAA ATT TTC CAA AAT GTG GAT GAC ACA CTG       240
Asp Phe Glu Glu Ala Lys Glu Ile Phe Gln Asn Val Asp Asp Thr Leu
 65              70                  75                  80

GCC TTC TGG TCC AAG CAC GTC GAC GGT GAC CAG TGC TTG GTC TTG CCC       288
Ala Phe Trp Ser Lys His Val Asp Gly Asp Gln Cys Leu Val Leu Pro
                 85                  90                  95

TTG GAG CAC CCG TGC GCC AGC CTG TGC TGC GGG CAC GGC ACG TGC ATC       336
Leu Glu His Pro Cys Ala Ser Leu Cys Cys Gly His Gly Thr Cys Ile
             100                 105                 110

GAC GGC ATC GGC AGC TTC AGC TGC GAC TGC CGC AGC GGC TGG GAG GGC       384
Asp Gly Ile Gly Ser Phe Ser Cys Asp Cys Arg Ser Gly Trp Glu Gly
             115                 120                 125

CGC TTC TGC CAG CGC GAG GTG AGC TTC CTC AAT TGC TCT CTG GAC AAC       432
Arg Phe Cys Gln Arg Glu Val Ser Phe Leu Asn Cys Ser Leu Asp Asn
 130                 135                 140

GGC GGC TGC ACG CAT TAC TGC CTA GAG GAG GTG GGC TGG CGG CGC TGT       480
Gly Gly Cys Thr His Tyr Cys Leu Glu Glu Val Gly Trp Arg Arg Cys
 145             150                 155                 160

AGC TGT GCG CCT GGC TAC AAG CTG GGG GAC GAC CTC CTG CAG TGT CAC       528
Ser Cys Ala Pro Gly Tyr Lys Leu Gly Asp Asp Leu Leu Gln Cys His
                 165                 170                 175

CCC GCA GTG AAG TTC CCT TGT GGG AGG CCC TGG AAG CGG ATG GAG AAG       576
Pro Ala Val Lys Phe Pro Cys Gly Arg Pro Trp Lys Arg Met Glu Lys
             180                 185                 190

AAG CGC AGT CAC CTG AAA CGA GAC ACA GAA GAC CAA GAA GAC CAA GTA       624
Lys Arg Ser His Leu Lys Arg Asp Thr Glu Asp Gln Glu Asp Gln Val
             195                 200                 205

GAT CCG CGG CTC ATT GAT GGG AAG ATG ACC AGG CGG GGA GAC AGC CCC       672
Asp Pro Arg Leu Ile Asp Gly Lys Met Thr Arg Arg Gly Asp Ser Pro
 210                 215                 220

TGG CAG GTG GTC CTG CTG GAC TCA AAG AAG AAG CTG GCC TGC GGG GCA       720
Trp Gln Val Val Leu Leu Asp Ser Lys Lys Lys Leu Ala Cys Gly Ala
 225                 230                 235                 240

GTG CTC ATC CAC CCC TCC TGG GTG CTG ACA GCG GCC CAC TGC ATG GAT       768
Val Leu Ile His Pro Ser Trp Val Leu Thr Ala Ala His Cys Met Asp
                 245                 250                 255

GAG TCC AAG AAG CTC CTT GTC AGG CTT GGA GAG TAT GAC CTG CGG CGC       816
Glu Ser Lys Lys Leu Leu Val Arg Leu Gly Glu Tyr Asp Leu Arg Arg
             260                 265                 270

TGG GAG AAG TGG GAG CTG GAC CTG GAC ATC AAG GAG GTC TTC GTC CAC       864
Trp Glu Lys Trp Glu Leu Asp Leu Asp Ile Lys Glu Val Phe Val His
             275                 280                 285

CCC AAC TAC AGC AAG AGC ACC ACC GAC AAT GAC ATC GCA CTG CTG CAC       912
Pro Asn Tyr Ser Lys Ser Thr Thr Asp Asn Asp Ile Ala Leu Leu His
 290                 295                 300

CTG GCC CAG CCC GCC ACC CTC TCG CAG ACC ATA GTG CCC ATC TGC CTC       960
Leu Ala Gln Pro Ala Thr Leu Ser Gln Thr Ile Val Pro Ile Cys Leu
 305                 310                 315                 320

CCG GAC AGC GGC CTT GCA GAG CGC GAG CTC AAT CAG GCC GGC CAG GAG      1008
Pro Asp Ser Gly Leu Ala Glu Arg Glu Leu Asn Gln Ala Gly Gln Glu
```

```
             325                 330                 335
ACC CTC GTG ACG GGC TGG GGC TAC CAC AGC AGC CGA GAG AAG GAG GCC      1056
Thr Leu Val Thr Gly Trp Gly Tyr His Ser Ser Arg Glu Lys Glu Ala
            340                 345                 350

AAG AGA AAC CGC ACC TTC GTC CTC AAC TTC ATC AAG ATT CCC GTG GTC      1104
Lys Arg Asn Arg Thr Phe Val Leu Asn Phe Ile Lys Ile Pro Val Val
            355                 360                 365

CCG CAC AAT GAG TGC AGC GAG GTC ATG AGC AAC ATG GTG TCT GAG AAC      1152
Pro His Asn Glu Cys Ser Glu Val Met Ser Asn Met Val Ser Glu Asn
            370                 375                 380

ATG CTG TGT GCG GGC ATC CTC GGG GAC CGG CAG GAT GCC TGC GAG GGC      1200
Met Leu Cys Ala Gly Ile Leu Gly Asp Arg Gln Asp Ala Cys Glu Gly
385                 390                 395                 400

GAC AGT GGG GGG CCC ATG GTC GCC TCC TTC CAC GGC ACC TGG TTC CTG      1248
Asp Ser Gly Gly Pro Met Val Ala Ser Phe His Gly Thr Trp Phe Leu
            405                 410                 415

GTG GGC CTG GTG AGC TGG GGT GAG GGC TGT GGG CTC CTT CAC AAC TAC      1296
Val Gly Leu Val Ser Trp Gly Glu Gly Cys Gly Leu Leu His Asn Tyr
            420                 425                 430

GGC GTT TAC ACC AAA GTC AGC CGC TAC CTC GAC TGG ATC CAT GGG CAC      1344
Gly Val Tyr Thr Lys Val Ser Arg Tyr Leu Asp Trp Ile His Gly His
            435                 440                 445

ATC AGA GAC AAG GAA GCC CCC CAG AAG AGC TGG GCA CCTTAG              1386
Ile Arg Asp Lys Glu Ala Pro Gln Lys Ser Trp Ala
450                 455                 460

(2) INFORMATION FOR SEQ ID NO:4:

(i) SEQUENCE CHARACTERISTICS:
        (A) LENGTH: 460 amino acids
        (B) TYPE: amino acid
        (D) TOPOLOGY: linear (ii) MOLECULE TYPE: protein (xi) SEQUENCE DESCRIPTION: SEQ ID NO:4:

Met Trp Gln Leu Thr Ser Leu Leu Phe Val Ala Thr Trp Gly Ile
1               5                   10                  15

Ser Gly Thr Pro Ala Pro Leu Asp Ser Val Phe Ser Ser Glu Arg
                20                  25                  30

Ala His Gln Val Leu Arg Ile Arg Lys Arg Ala Asn Ser Phe Leu Glu
            35                  40                  45

Glu Leu Arg His Ser Ser Leu Glu Arg Glu Cys Ile Glu Glu Ile Cys
    50                  55                  60

Asp Phe Glu Glu Ala Lys Glu Ile Phe Gln Asn Val Asp Asp Thr Leu
65                  70                  75                  80

Ala Phe Trp Ser Lys His Val Asp Gly Asp Gln Cys Leu Val Leu Pro
                85                  90                  95

Leu Glu His Pro Cys Ala Ser Leu Cys Cys Gly His Gly Thr Cys Ile
            100                 105                 110

Asp Gly Ile Gly Ser Phe Ser Cys Asp Cys Arg Ser Gly Trp Glu Gly
            115                 120                 125

Arg Phe Cys Gln Arg Glu Val Ser Phe Leu Asn Cys Ser Leu Asp Asn
            130                 135                 140

Gly Gly Cys Thr His Tyr Cys Leu Glu Glu Val Gly Trp Arg Arg Cys
145                 150                 155                 160

Ser Cys Ala Pro Gly Tyr Lys Leu Gly Asp Asp Leu Leu Gln Cys His
                165                 170                 175

Pro Ala Val Lys Phe Pro Cys Gly Arg Pro Trp Lys Arg Met Glu Lys
```

```
            180             185             190
Lys Arg Ser His Leu Lys Arg Asp Thr Glu Asp Gln Glu Asp Gln Val
            195             200             205
Asp Pro Arg Leu Ile Asp Gly Lys Met Thr Arg Arg Gly Asp Ser Pro
210             215             220
Trp Gln Val Val Leu Leu Asp Ser Lys Lys Leu Ala Cys Gly Ala
225             230             235             240
Val Leu Ile His Pro Ser Trp Val Leu Thr Ala Ala His Cys Met Asp
            245             250             255
Glu Ser Lys Lys Leu Leu Val Arg Leu Gly Glu Tyr Asp Leu Arg Arg
            260             265             270
Trp Glu Lys Trp Glu Leu Asp Leu Asp Ile Lys Glu Val Phe Val His
            275             280             285
Pro Asn Tyr Ser Lys Ser Thr Thr Asp Asn Asp Ile Ala Leu Leu His
            290             295             300
Leu Ala Gln Pro Ala Thr Leu Ser Gln Thr Ile Val Pro Ile Cys Leu
305             310             315             320
Pro Asp Ser Gly Leu Ala Glu Arg Glu Leu Asn Gln Ala Gly Gln Glu
            325             330             335
Thr Leu Val Thr Gly Trp Gly Tyr His Ser Ser Arg Glu Lys Glu Ala
            340             345             350
Lys Arg Asn Arg Thr Phe Val Leu Asn Phe Ile Lys Ile Pro Val Val
            355             360             365
Pro His Asn Glu Cys Ser Glu Val Met Ser Asn Met Val Ser Glu Asn
            370             375             380
Met Leu Cys Ala Gly Ile Leu Gly Asp Arg Gln Asp Ala Cys Glu Gly
385             390             395             400
Asp Ser Gly Gly Pro Met Val Ala Ser Phe His Gly Thr Trp Phe Leu
            405             410             415
Val Gly Leu Val Ser Trp Gly Glu Gly Cys Gly Leu Leu His Asn Tyr
            420             425             430
Gly Val Tyr Thr Lys Val Ser Arg Tyr Leu Asp Trp Ile His Gly His
            435             440             445
Ile Arg Asp Lys Glu Ala Pro Gln Lys Ser Trp Ala
450             455             460

(2) INFORMATION FOR SEQ ID NO:5:

(i) SEQUENCE CHARACTERISTICS:
        (A) LENGTH: 10807 base pairs
        (B) TYPE: nucleic acid
        (C) STRANDEDNESS: single
        (D) TOPOLOGY: linear (xi) SEQUENCE DESCRIPTION: SEQ ID NO:5:

ACGCGTGTCG ACCTGCAGGT CAACGGATCT CTGTGTCTGT TTTCATGTTA GTACCACACT    60

GTTTTGGTGG CTGTAGCTTT CAGCTACAGT CTGAAGTCAT AAAGCCTGGT ACCTCCAGCT   120

CTGTTCTCTC TCAAGATTGT GTTCTGCTGT TTGGGTCTTT AGTGTCTCCA CACAATTTTT   180

AGAATTGTTT GTTCTAGTTC TGTGAAAAAT GATGCTGGTA TTTTGATAAG GATTGCATTG   240

AATCTGTAAA GCTACAGATA TAGTCATTGG GTAGTACAGT CACTTTAACA ATATTAACTC   300

TTCACATCTG TGAGCATGAT ATATTTTCCC CCTCTATATC ATCTTCAATT CCTCCTATCA   360

GTTTCTTTCA TTGCAGTTTT CTGAGTACAG GTCTTACACC TCCTTGGTTA GAGTCATTCC   420

TCAGTATTTT ATTCCTTTGA TACAATTGTG AATGAGGTAA TTTTCTTAGT TTCTCTTTCT   480
```

-continued

| | |
|---|---|
| GATAGCTCAT TGTTAGTGTA TATATAGAAA AGCAACAGAT TTCTATGTAT TAATTTTGTA | 540 |
| TCCTGCAACA GATTTCTATG TATTAATTTT GTATCCTGCT ACTTTACGGA ATTCACTTAT | 600 |
| TAGCTTTTTG GTGACATCTT GAGGATTTTC TGAAGAAAAT GGCATGGTAT GGTAGGACAA | 660 |
| GGTGTCATGT CATCTGCAAA CAGTGGCAGT TTTCCTTCTT CCCTTCCAAC CTGGATTTCT | 720 |
| TTGATTTCTT TCTGTCTGAG TACGACTAGG ATTCCCAATA CTATACCGAA TAAAAGTGGC | 780 |
| AAGAGTGGAC ATCCTTGTCT TATTTTTCTG ACCTTAGAGG AAATGCTTTC AGTTTTTCAC | 840 |
| CATTAATTAT AATGTTTACT GTGGGCTTGT CATATGTGGC CTTCATTATA TGGAGGTCTA | 900 |
| TTCCCTCTAT ACCCACCTTG TTGAGAGTTT TTATCATAAA AGTATGTTGA ATTTTGTCAA | 960 |
| AAGTTTTTCC TGCATCTATT GAGATGATTT TTACTCTTCA ATTCATTAAT GATTTTTATT | 1020 |
| CTTCATTTTG TTAATGATTT CCATTCTTCA ATTTGTTAAC GTGGTATATC ACATTGATTG | 1080 |
| ATTTGTGGAT ACCTTTGTAT CCCTGGGATA AACCTCACTT GATCATGAGC TTTCAATGTA | 1140 |
| TTTTTGAATT CACTTTGCTA ATATTCTGTT GGGTATTTTT GCATCTCTAT TCATCAATGA | 1200 |
| TATTGGCCTA AGAAAGGTTT TGTCTGGTTT TAGTATCAGG GTGATGCTGG CCTCATAGAG | 1260 |
| AGAGTTTAGA AGCATTTCCT CCTCTTTGAT TTTTCGGAAT AGTTTGAGTA GGATAGGTAT | 1320 |
| TAACTCTTCT TTAAATGTTT GGGGACTTCC CTGGTGAGCC GGTGGTTGAG AATCCGCCTC | 1380 |
| AGGGATGTGG GTTTGATCCC TGGTCAGGGA ACCATTAATA AGATCCCACA TGCTGCAGGC | 1440 |
| AACAAGCCCC CAAGCTGCAA CCACTGAGCT GCAACCGCTG CAGTGCCCAC AGGCCACGAC | 1500 |
| CAGAGAAAGC CCACATACAG CAGGGAAGAC CCAGCACAAC CGGAAAAAGG AGTTTGGTGG | 1560 |
| AATACAGCTG TGAAGCCGTC TGGTCCTGGA CTCCTGCTTG AGGGAATTTT TTAAAAATTA | 1620 |
| TTGATTCAAT TCATTACTG GTAACTGGTC TGTTCATATT TTCTATTTCT TCCGGGTTCA | 1680 |
| GTCTTGGGAG ATTGTACATG CCTAGGAATG TGTCCGTTTC TTCTAGGTTG TCCATTTTAT | 1740 |
| TGGACATGCA TGGGAGCACA CAGCACCGAC CAGCGAGACT CATGCTGGCT TCCTGGGGCC | 1800 |
| AGGCTGGGGC CCCAAGCAGC ATGGCATCCT AGAGTGTGTG AAAGCCCACT GACCCTGCCC | 1860 |
| AGCCCCACAA TTTCATTCTG AGAAGTGATT CCTTGCTTCT GCACTTACAG GCCCAGGATC | 1920 |
| TGACCTGCTT CTGAGGAGCA GGGGTTTTGG CAGGACGGGG AGATGCTGAG AGCCGACGGG | 1980 |
| GGTCCAGGTC CCCTCCCAGG CCCCCCTGTC TGGGGCAGCC CTTGGGAAAG ATTGCCCCAG | 2040 |
| TCTCCCTCCT ACAGTGGTCA GTCCCAGCTG CCCCAGGCCA GAGCTGCTTT ATTTCCGTCT | 2100 |
| CTCTCTCTGG ATGGTATTCT CTGGAAGCTG AAGGTTCCTG AAGTTATGAA TAGCTTTGCC | 2160 |
| CTGAAGGGCA TGGTTTGTGG TCACGGTTCA CAGGAACTTG GGAGACCCTG CAGCTCAGAC | 2220 |
| GTCCCGAGAT TGGTGGCACC CAGATTTCCT AAGCTCGCTG GGAACAGGG CGCTTGTTTC | 2280 |
| TCCCTGGCTG ACCTCCCTCC TCCCTGCATC ACCCAGTTCT GAAAGCAGAG CGGTGCTGGG | 2340 |
| GTCACAGCCT CTCGCATCTA ACGCCGGTGT CCAAACCACC CGTGCTGGTG TTCGGGGGGC | 2400 |
| TACCTATGGG GAAGGGCTTC TCACTGCAGT GGTGCCCCCC GTCCCTCTG AGATCAGAAG | 2460 |
| TCCCAGTCCG GACGTCAAAC AGGCCGAGCT CCCTCCAGAG GCTCCAGGGA GGGATCCTTG | 2520 |
| CCCCCCGCT GCTGCCTCCA GCTCCTGGTG CCGCACCCTT GAGCCTGATC TTGTAGACGC | 2580 |
| CTCAGTCTAG TCTCTGCCTC CGTGTTCACA CGCCTTCTCC CCATGTCCCC TCCGTGTCCC | 2640 |
| CGTTTTCTCT CACAAGGACA CCGGACATTA GATTAGCCCC TGTTCCAGCC TCACCTGAAC | 2700 |
| AGCTCACATC TGTAAAGACC TAGATTCCAA ACAAGATTCC AACCTGAAGT TCCCGGTGGA | 2760 |
| TGTGAGTTCT GGGGCGACAT CCTTCAACCC CATCACAGCT TGCAGTTCAT CGCAAAACAT | 2820 |
| GGAACCTGGG GTTATCGTA AAACCCAGGT TCTTCATGAA ACACTGAGCT TCGAGGCTTG | 2880 |

```
TTGCAAGAAT TAAAGGTGCT AATACAGATC AGGGCAAGGA CTGAAGCTGG CTAAGCCTCC    2940

TCTTTCCATC ACAGGAAAGG GGGGCCTGGG GGCGGCTGGA GGTCTGCTCC CGTGAGTGAG    3000

CTCTTTCCTG CTACAGTCAC CAACAGTCTC TCTGGGAAGG AAACCAGAGG CCAGAGAGCA    3060

AGCCGGAGCT AGTTTAGGAG ACCCCTGAAC CTCCACCCAA GATGCTGACC AGCCAGCGGG    3120

CCCCCTGGAA AGACCCTACA GTTCAGGGGG AAGAGGGGC TGACCCGCCA GGTCCCTGCT     3180

ATCAGGAGAC ATCCCCGCTA TCAGGAGATT CCCCCACCTT GCTCCCGTTC CCCTATCCCA    3240

ATACGCCCAC CCCACCCCTG TGATGAGCAG TTTAGTCACT TAGAATGTCA ACTGAAGGCT    3300

TTTGCATCCC CTTTGCCAGA GGCACAAGGC ACCCACAGCC TGCTGGGTAC CGACGCCCAT    3360

GTGGATTCAG CCAGGAGGCC TGTCCTGCAC CCTCCCTGCT CGGGCCCCCT CTGTGCTCAG    3420

CAACACACCC AGCACCAGCA TTCCCGCTGC TCCTGAGGTC TGCAGGCAGC TCGCTGTAGC    3480

CTGAGCGGTG TGGAGGGAAG TGTCCTGGGA GATTTAAAAT GTGAGAGGCG GGAGGTGGGA    3540

GGTTGGGCCC TGTGGGCCTG CCCATCCCAC GTGCCTGCAT TAGCCCCAGT GCTGCTCAGC    3600

CGTGCCCCCG CCGCAGGGGT CAGGTCACTT TCCCGTCCTG GGGTTATTAT GACTCTTGTC    3660

ATTGCCATTG CCATTTTTGC TACCCTAACT GGGCAGCAGG TGCTTGCAGA GCCCTCGATA    3720

CCGACCAGGT CCTCCCTCGG AGCTCGACCT GAACCCCATG TCACCCTTGC CCCAGCCTGC    3780

AGAGGGTGGG TGACTGCAGA GATCCCTTCA CCCAAGGCCA CGGTCACATG GTTTGGAGGA    3840

GCTGGTGCCC AAGGCAGAGG CCACCCTCCA GGACACACCT GTCCCAGTG CTGGCTCTGA     3900

CCTGTCCTTG TCTAAGAGGC TGACCCCGGA AGTGTTCCTG GCACTGGCAG CCAGCCTGGA    3960

CCCAGAGTCC AGACACCCAC CTGTGCCCCC GCTTCTGGGG TCTACCAGGA ACCGTCTAGG    4020

CCCAGAGGGG ACTTCCTGCT TGGCCTTGGA TGGAAGAAGG CCTCCTATTG TCCTCGTAGA    4080

GGAAGCCACC CCGGGGCCTG AGGATGAGCC AAGTGGGATT CCGGGAACCG CGTGGCTGGG    4140

GGCCCAGCCC GGGCTGGCTG GCCTGCATGC CTCCTGTATA AGGCCCCAAG CCTGCTGTCT    4200

CAGCCCTCCA CTCCCTGCAG AGCTCAGAAG CACGACCCCA GGGATATCCC TGCAGCCATG    4260

AAGTGCCTCC TGCTTGCCCT GGGCCTGGCC CTCGCCTGTG GCGTCAGGC CATCATCGTC     4320

ACCCAGACCA TGAAAGGCCT GGACATCCAG AAGGTTCGAG GGTTGGCCGG GTGGGTGAGT    4380

TGCAGGGCGG GCAGGGGAGC TGGGCCTCAG AGAGCCAAGA GAGGCTGTGA CGTTGGGTTC    4440

CCATCAGTCA GCTAGGGCCA CCTGACAAAT CCCCGCTGGG GCAGCTTCAA CCAGGCGTTC    4500

ACTGTCTTGC ATTCTGGAGG CTGGAAGCCC AAGATCCAGG TGTTGGCAGG GCTGGCTTCT    4560

CCTGCGGCCG CTCTCTGGGG AGCAGACGGC CGTCTTCTCC AGTCCTCTGC GCGCCCTGAT    4620

TTCCTCTTCC TGTGAGGCCA CCAGGCCTGC TGGAAACACG CCTGCCTGCG CAGCTTCACA    4680

CGACCTTTGT CATCTCTTTA AAGGCCATGT CTCCAGAGTC ATGTGTTGAA GTTCTGGGGG    4740

TTAGTGGGAC ACAGTTCAGC CCCTAAAAGA GTCTCTCTGC CCCTCAAATT TTCCCCACCT    4800

CCAGCCATGT CTCCCCAAGA TCCAAATGTT GCTACATGTG GGGGGCTCA TCTGGGTCCC     4860

TCTTTGGGTT CAGTGTGAGT CTGGGGAGAG CATTCCCCAG GGTGCAGAGT TGGGGGAGT    4920

ATCTCAGGGC TGCCCAGGCC GGGGTGGGAC AGAGAGCCCA CTGTGGGGCT GGGGGCCCCT    4980

TCCCACCCCC AGAGTGCAAC TCAAGGTCCC TCTCCAGGTG GCGGGGACTT GGCACTCCTT    5040

GGCTATGGCG GCCAGCGACA TCTCCCTGCT GGATGCCCAG AGTGCCCCCC TGAGAGTGTA    5100

CGTGGAGGAG CTGAAGCCCA CCCCCGAGGG CAACCTGGAG ATCCTGCTGC AGAAATGGTG    5160

GGCGTCTCTC CCCAACATGG AACCCCACT CCCCAGGGCT GTGGACCCCC CGGGGGGTGG     5220

GGTGCAGGAG GGACCAGGGC CCCAGGGCTG GGGAAGAGGG CTCAGAGTTT ACTGGTACCC    5280
```

```
GGCGCTCCAC CCAAGGCTGC CCACCCAGGG CTTTTTTTTT TTTTAAACTT TTATTAATTT     5340

GATGCTTCAG AACATCATCA AACAAATGAA CATAAAACAT TCATTTTTGT TTACTTGGAA     5400

GGGGAGATAA AATCCTCTGA AGTGGAAATG CATAGCAAAG ATACATACAA TGAGGCAGGT     5460

ATTCTGAATT CCCTGTTAGT CTGAGGATTA CAAGTGTATT TGAGCAACAG AGAGACATTT     5520

TCATCATTTC TAGTCTGAAC ACCTCAGTAT CTAAAATGAA CAAGAAGTCC TGGAAACGAA     5580

GCAGTGTGGG GATAGGCCCG TGTGAAGGCT GCTGGGAGGC AGCAGACCTG GGTCTTCGGG     5640

CTCAAGCAGT TCCCGCTACC AGCCCTGTCC ACCTCAGACG GGGGTCAGGG TGCAGGAGAG     5700

AGCTGGATGG GTGTGGGGGC AGAGATGGGG ACCTGAACCC CAGGGCTGCC TTTTGGGGGT     5760

GCCTGTGGTC AAGGCTCTCC CTGACCTTTT CTCTCTGGCT TCATCTGACT TCTCCTGGCC     5820

CATCCACCCG GTCCCCTGTG GCCTGAGGTG ACAGTGAGTG CGCCGAGGCT AGTTGGCCAG     5880

CTGGCTCCTA TGCCCATGCC ACCCCCCTCC AGCCCTCCTG GCCAGCTTC TGCCCCTGGC      5940

CCTCAGTTCA TCCTGATGAA AATGGTCCAT GCCAATGGCT CAGAAAGCAG CTGTCTTTCA     6000

GGGAGAACGG CGAGTGTGCT CAGAAGAAGA TTATTGCAGA AAAAACCAAG ATCCCTGCGG     6060

TGTTCAAGAT CGATGGTGAG TCCGGTCCC TGGGGACAC CCACCACCCC CGCCCCCGGG       6120

GACTGTGGAC AGGTTCAGGG GGCTGGCGTC GGGCCCTGGG ATGCTAAGGG ACTGGTGGTG     6180

ATGAAGACAC TGCCTTGACA CCTGCTTCAC TTGCCTCCCC TGCCACCTGC CCGGGGCCTT     6240

GGGGCGGTGG CCATGGGCAG GTCCCGGCTG GCGGGCTAAC CCACCAGGGT GACACCCGAG     6300

CTCTCTTTGC TGGGGGGCGG GCGGTGCTCT GGGCCCTCAG GCTGAGCTCA GGAGGTACCT     6360

GTGCCCTCCC AGGGGTAACC GAGAGCCGTT GCCCACTCCA GGGGCCCAGG TGCCCCACGA     6420

CCCCAGCCCG CTCCACAGCT CCTTCATCTC CTGGAGACAA ACTCTGTCCG CCCTCGCTCA     6480

TTCACTTGTT CGTCCTAAAT CCGAGATGAT AAAGCTTCGA GGGGGGGTTG GGGTTCCATC     6540

AGGGCTGCCC TTCCGCCGGG CAGCCTGGGC ACATCTGCC CTTGGCCCCC TCAGGACTCA      6600

CTCTGACTGG AGGCCCTGCA CTGACTGACG CCAGGGTGCC CAGCCCAGGG TCTCTGGCGC     6660

CATCCAGCTG CACTGGGTTT GGGTGCTGGT CCTGCCCCCA AGCTGCCCGG ACACCACAGG    6720

CAGCCGGGGC TGCCCACTGG CCTCGGTCAG GGTGAGCCCC AGCTGCCCCC GCTCAGGGCT     6780

TGCCCCGACA ATGACCCCAT CCTCAGGACG CACCCCCCTT CCCTTGCTGG GCAGTGTCCA     6840

GCCCCACCCG AGATCGGGGG AAGCCCTATT TCTTGACAAC TCCAGTCCCT GGGGAGGGG     6900

GCCTCAGACT GAGTGGTGAG TGTTCCCAAG TCCAGGAGGT GGTGGAGGGT CCTGGCGGAT     6960

CCAGAGTTGA CAGTGAGGGC TTCCTGGGCC CCATGCGCCT GGCAGTGGCA GCAGGGAAGA    7020

GGAAGCACCA TTTCAGGGGT GGGGGATGCC AGAGGCGCTC CCCACCCCGT CTTCGCCGGG    7080

TGGTGACCCC GGGGGAGCCC CGCTGGTCGT GGAGGGTGCT GGGGGCTGAC TAGCAACCCC    7140

TCCCCCCCCG TTGGAACTCA CTTTTCTCCC GTCTTGACCG CGTCCAGCCT TGAATGAGAA     7200

CAAAGTCCTT GTGCTGGACA CCGACTACAA AAAGTACCTG CTCTTCTGCA TGGAAAACAG     7260

TGCTGAGCCC GAGCAAAGCC TGGCCTGCCA GTGCCTGGGT GGGTGCCAAC CCTGGCTGCC    7320

CAGGGAGACC AGCTGCGTGG TCCTTGCTGC AACAGGGGGT GGGGGGTGGG AGCTTGATCC    7380

CCAGGAGGAG GAGGGGTGGG GGGTCCCTGA GTCCCGCCAG GAGAGAGTGG TCGCATACCG    7440

GGAGCCAGTC TGCTGTGGGC CTGTGGGTGG CTGGGACGG GGGCCAGACA CACAGGCCGG      7500

GAGACGGGTG GGCTGCAGAA CTGTGACTGG TGTGACCGTC GCGATGGGGC CGGTGGTCAC    7560

TGAATCTAAC AGCCTTTGTT ACCGGGGAGT TTCAATTATT TCCAAAAATA AGAACTCAGG     7620

TACAAAGCCA TCTTTCAACT ATCACATCCT GAAAACAAAT GGCAGGTGAC ATTTTCTGTG     7680
```

-continued

```
CCGTAGCAGT CCCACTGGGC ATTTTCAGGG CCCCTGTGCC AGGGGGGCGC GGGCATCGGC    7740
GAGTGGAGGC TCCTGGCTGT GTCAGCCGGC CCAGGGGGAG GAAGGGACCC GGACAGCCAG    7800
AGGTGGGGGG CAGGCTTTCC CCCTGTGACC TGCAGACCCA CTGCACTGCC CTGGGAGGAA    7860
GGGAGGGGAA CTAGGCCAAG GGGGAAGGGC AGGTGCTCTG GAGGGCAAGG GCAGACCTGC    7920
AGACCACCCT GGGGAGCAGG GACTGACCCC CGTCCCTGCC CCATAGTCAG GACCCCGGAG    7980
GTGGACAACG AGGCCCTGGA GAAATTCGAC AAAGCCCTCA AGGCCCTGCC CATGCACATC    8040
CGGCTTGCCT TCAACCCGAC CCAGCTGGAG GGTGAGCACC CAGGCCCCGC CCTTCCCCAG    8100
GGCAGGAGCC ACCCGGCCCC GGGACGACCT CCTCCCATGG TGACCCCAG CTCCCCAGGC    8160
CTCCCAGGAG GAAGGGGTGG GGTGCAGCAC CCCGTGGGGG CCCCCTCCCC ACCCCCTGCC    8220
AGGCCTCTCT TCCCGAGGTG TCCAGTCCCA TCCTGACCCC CCCATGACTC TCCCTCCCCC    8280
ACAGGGCAGT GCCACGTCTA GGTGAGCCCC TGCCGGTGCC TCTGGGGTAA GCTGCCTGCC    8340
CTGCCCCACG TCCTGGGCAC ACACATGGGG TAGGGGGTCT TGGTGGGGCC TGGGACCCCA    8400
CATCAGGCCC TGGGGTCCCC CCTGTGAGAA TGGCTGGAAG CTGGGGTCCC TCCTGGCGAC    8460
TGCAGAGCTG GCTGGCCGCG TGCCACTCTT GTGGGTGACC TGTGTCCTGG CCTCACACAC    8520
TGACCTCCTC CAGCTCCTTC CAGCAGAGCT AAGGCTAAGT GAGCCAGAAT GGTACCTAAG    8580
GGGAGGCTAG CGGTCCTTCT CCCGAGGAGG GGCTGTCCTG GAACCACCAG CCATGGAGAG    8640
GCTGGCAAGG GTCTGGCAGG TGCCCCAGGA ATCACAGGGG GGCCCCATGT CCATTTCAGG    8700
GCCCGGGAGC CTTGGACTCC TCTGGGGACA GACGACGTCA CCACCGCCCC CCCCCCATCA    8760
GGGGGACTAG AAGGGACCAG GACTGCAGTC ACCCTTCCTG GGACCCAGGC CCCTCCAGGC    8820
CCCTCCTGGG GCTCCTGCTC TGGGCAGCTT CTCCTTCACC AATAAAGGCA TAAACCTGTG    8880
CTCTCCCTTC TGAGTCTTTG CTGGACGACG GCAGGGGGT GGAGAAGTGG TGGGGAGGGA    8940
GTCTGGCTCA GAGGATGACA GCGGGCTGG GATCCAGGGC GTCTGCATCA CAGTCTTGTG    9000
ACAACTGGGG GCCCACACAC ATCACTGCGG CTCTTTGAAA CTTTCAGGAA CCAGGGAGGG    9060
ACTCGGCAGA GACATCTGCC AGTTCACTTG GAGTGTTCAG TCAACACCCA AACTCGACAA    9120
AGGACAGAAA GTGGAAAATG GCTGTCTCTT AGTCTAATAA ATATTGATAT GAAACTCAAG    9180
TTGCTCATGG ATCAATATGC CTTTATGATC CAGCCAGCCA CTACTGTCGT ATCAACTCAT    9240
GTACCCAAAC GCACTGATCT GTCTGGCTAA TGATGAGAGA TTCCCAGTAG AGAGCTGGCA    9300
AGAGGTCACA GTGAGAACTG TCTGCACACA CAGCAGAGTC CACCAGTCAT CCTAAGGAGA    9360
TCAGTCCTGG TGTTCATTGG AGGACTGATG TTGAAGCTGA AACTCCAATG CTTTGGCCAC    9420
CTGATGTGAA GAGCTGACTC ATTTGAAAAG ACCCTGATGC TGGGAAAGAT TGAGGGCAGG    9480
AGGAGAAGGG GACGACAGAG GATGAGATGG TTGGATGGCA TCACCAACAC AATGGACATG    9540
GGTTTGGGTG GACTCCAGGA GTTGGTGATG GACAGGGAGG CCTGGCGTGC TACGGAAGCG    9600
GTTTATGGGG TCACAAAGAC TGAGTGACTG AACTGAGCTG AACTGAATGG AAATGAGGTA    9660
TACAGCAAAG TGGGGATTTT TTAGATAATA AGAATATACA CATAACATAG TGTATACTCA    9720
TATTTTTATG CATACCTGAA TGCTCAGTCA CTCAGTCGTA TCTGACTCTG TGACCTATGG    9780
ACCGTAGCCT TCCAGGTTTC TTCTGTCCAC AGAATTCTCC AAGGCAAGAA TACTGGAGTG    9840
GGTAGCCATT TCCTCCTCCA GGGGATCCTC CCGACCCAGG GATTGAACCG GCATCTCCTG    9900
TATTGGCAGG TGGATTCTTT ACCACTGTGC CACCAGGGAA GCCCGTGTTA CTCTCTATGT    9960
CCCACTTAAT TACCAAAGCT GCTCCAAGAA AAAGCCCCTG TGCCCTCTGA GCTTCCCGGC   10020
CTGCAGAGGG TGGTGGGGGT AGACTGTGAC CTGGGAACAC CCTCCCGCTT CAGGACTCCC   10080
```

```
GGGCCACGTG ACCCACAGTC CTGCAGACAG CCGGGTAGCT CTGCTCTTCA AGGCTCATTA    10140

TCTTTAAAAA AAACTGAGGT CTATTTTGTG ACTTCGCTGC CGTAACTTCT GAACATCCAG    10200

TGCGATGGAC AGGACCTCCT CCCCAGGCCT CAGGGGCTTC AGGGAGCCAG CCTTCACCTA    10260

TGAGTCACCA GACACTCGGG GGTGGCCCCG CCTTCAGGGT GCTCACAGTC TTCCCATCGT    10320

CCTGATCAAA GAGCAAGACC AATGACTTCT TAGGAGCAAG CAGACACCCA CAGGACACTG    10380

AGGTTCACCA GAGCTGAGCT GTCCTTTTGA ACCTAAAGAC ACACAGCTCT CGAAGGTTTT    10440

CTCTTTAATC TGGATTTAAG GCCTACTTGC CCCTCAAGAG GGAAGACAGT CCTGCATGTC    10500

CCCAGGACAG CCACTCGGTG GCATCCGAGG CCACTTAGTA TTATCTGACC GCACCCTGGA    10560

ATTAATCGGT CCAAACTGGA CAAAAACCTT GGTGGGAAGT TTCATCCCAG AGGCCTCAAC    10620

CATCCTGCTT TGACCACCCT GCATCTTTTT TTCTTTTATG TGTATGCATG TATATATATA    10680

TATATATTTT TTTTTTTTTC ATTTTTTGGC TGTGCTGGCT GTTCGTTGCA GTTCGGTGCG    10740

CAGGCTTCTC TCTAGTTTCT CTCTAGTCTT CTCTTATCAC AGAGCAGTCT CTAGACGATC    10800

GACGCGT                                                              10807

(2) INFORMATION FOR SEQ ID NO:6:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (xi) SEQUENCE DESCRIPTION: SEQ ID NO:6:

AATTCCGATC GACGCGTCGA CGATATACTC TAGACGATCG ACGCGTA                  47

(2) INFORMATION FOR SEQ ID NO:7:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (xi) SEQUENCE DESCRIPTION: SEQ ID NO:7:

AAGCTACGCG TCGATCGTCT AGAGTATATC GTCGACGCGT CGATCGG                  47

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:8:

TGGATCCCCT GCCGGTGCCT CTGG                                           24

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:9:

AACGCGTCAT CCTCTGTGAG CCAG                                           24

(2) INFORMATION FOR SEQ ID NO:10:
```

```
        (i) SEQUENCE CHARACTERISTICS:
            (A) LENGTH: 10 base pairs
            (B) TYPE: nucleic acid
            (C) STRANDEDNESS: single
            (D) TOPOLOGY: linear (vii) IMMEDIATE SOURCE:
            (B) CLONE: ZC6839

(xi) SEQUENCE DESCRIPTION: SEQ ID NO:10:

ACTACGTAGT                                                              10

(2) INFORMATION FOR SEQ ID NO:11:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (vii) IMMEDIATE SOURCE:
            (B) CLONE: ZC962

(xi) SEQUENCE DESCRIPTION: SEQ ID NO:11:

AGTCACCTGA GAAGAAAACG AGACA                                             25

(2) INFORMATION FOR SEQ ID NO:12:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (vii) IMMEDIATE SOURCE:
            (B) CLONE: ZC6303

(xi) SEQUENCE DESCRIPTION: SEQ ID NO:12:

ATTTGCGGCC GCCTGCAGCC ATGTGGCAGC TCACAAGCCT CCTGC                       45

(2) INFORMATION FOR SEQ ID NO:13:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (vii) IMMEDIATE SOURCE:
            (B) CLONE: ZC6337

(xi) SEQUENCE DESCRIPTION: SEQ ID NO:13:

CAGGAAGGAG TTGGCGCGCT TGCGCCGTTG CAGCACCTGG TGGGC                       45

(2) INFORMATION FOR SEQ ID NO:14:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (vii) IMMEDIATE SOURCE:
            (B) CLONE: ZC6306

(xi) SEQUENCE DESCRIPTION: SEQ ID NO:14:

CTTCTTCCTG AATTCTGTTT CTTGC                                             25

(2) INFORMATION FOR SEQ ID NO:15:
```

(i) SEQUENCE CHARACTERISTICS:
    (A) LENGTH: 28 base pairs
    (B) TYPE: nucleic acid
    (C) STRANDEDNESS: single
    (D) TOPOLOGY: linear (vii) IMMEDIATE SOURCE:
    (B) CLONE: ZC6338

(xi) SEQUENCE DESCRIPTION: SEQ ID NO:15:

CGGATCCGCA AGCGCGCCAA CTCCTTCC                                        28

(2) INFORMATION FOR SEQ ID NO:16:

(i) SEQUENCE CHARACTERISTICS:
    (A) LENGTH: 28 base pairs
    (B) TYPE: nucleic acid
    (C) STRANDEDNESS: single
    (D) TOPOLOGY: linear (vii) IMMEDIATE SOURCE:
    (B) CLONE: ZC6373

(xi) SEQUENCE DESCRIPTION: SEQ ID NO:16:

AAAGTAAAAA AAGATCTAAA AATTTAAC                                        28

(2) INFORMATION FOR SEQ ID NO:17:

(i) SEQUENCE CHARACTERISTICS:
    (A) LENGTH: 32 base pairs
    (B) TYPE: nucleic acid
    (C) STRANDEDNESS: single
    (D) TOPOLOGY: linear (vii) IMMEDIATE SOURCE:
    (B) CLONE: ZC6305

(xi) SEQUENCE DESCRIPTION: SEQ ID NO:17:

GTGTCTCGTT TTCTTCTTAA GTGACTGCGC TT                                   32

(2) INFORMATION FOR SEQ ID NO:18:

(i) SEQUENCE CHARACTERISTICS:
    (A) LENGTH: 49 base pairs
    (B) TYPE: nucleic acid
    (C) STRANDEDNESS: single
    (D) TOPOLOGY: linear (vii) IMMEDIATE SOURCE:
    (B) CLONE: ZC6302

(xi) SEQUENCE DESCRIPTION: SEQ ID NO:18:

TTAAGAAGAA AACGAGACAC AGAAGACCAA GAAGACCAAG TAGATCCGC                 49

(2) INFORMATION FOR SEQ ID NO:19:

(i) SEQUENCE CHARACTERISTICS:
    (A) LENGTH: 43 base pairs
    (B) TYPE: nucleic acid
    (C) STRANDEDNESS: single
    (D) TOPOLOGY: linear (vii) IMMEDIATE SOURCE:
    (B) CLONE: ZC6304

(xi) SEQUENCE DESCRIPTION: SEQ ID NO:19:

GGATCTACTT GGTCTTCTTG GTCTTCTGTG TCTCGTTTTC TTC                       43

(2) INFORMATION FOR SEQ ID NO:20:

(i) SEQUENCE CHARACTERISTICS:
        (A) LENGTH: 4 amino acids
        (B) TYPE: amino acid
        (D) TOPOLOGY: linear (xi) SEQUENCE DESCRIPTION: SEQ ID NO:20:

Arg Arg Lys Arg
1

(2) INFORMATION FOR SEQ ID NO:21:

(i) SEQUENCE CHARACTERISTICS:
        (A) LENGTH: 4 amino acids
        (B) TYPE: amino acid
        (D) TOPOLOGY: linear (xi) SEQUENCE DESCRIPTION: SEQ ID NO:21:

Lys Arg Lys Arg
1

(2) INFORMATION FOR SEQ ID NO:22:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO:22:

Ser His Leu Arg Arg Lys Arg Asp
1               5

(2) INFORMATION FOR SEQ ID NO:23:

(i) SEQUENCE CHARACTERISTICS:
        (A) LENGTH: 6763 base pairs
        (B) TYPE: nucleic acid
        (C) STRANDEDNESS: double
        (D) TOPOLOGY: linear (xi) SEQUENCE DESCRIPTION: SEQ ID NO:23:

```
ACGCGTCGAC CTGCAGGTCA ACGGATCTCT GTGTCTGTTT TCATGTTAGT ACCACACTGT      60

TTTGGTGGCT GTAGCTTTCA GCTACAGTCT GAAGTCATAA AGCCTGGTAC CTCCAGCTCT     120

GTTCTCTCTC AAGATTGTGT TCTGCTGTTT GGGTCTTTAG TGTCTCCACA CAATTTTTAG     180

AATTGTTTGT TCTAGTTCTG TGAAAAATGA TGCTGGTATT TTGATAAGGA TTGCATTGAA     240

TCTGTAAAGC TACAGATATA GTCATTGGGT AGTACAGTCA CTTTAACAAT ATTAACTCTT     300

CACATCTGTG AGCATGATAT ATTTTCCCCC TCTATATCAT CTTCAATTCC TCCTATCAGT     360

TTCTTTCATT GCAGTTTTCT GAGTACAGGT CTTACACCTC CTTGGTTAGA GTCATTCCTC     420

AGTATTTTAT TCCTTTGATA CAATTGTGAA TGAGGTAATT TTCTTAGTTT CTCTTTCTGA     480

TAGCTCATTG TTAGTGTATA TATAGAAAAG CAACAGATTT CTATGTATTA ATTTTGTATC     540

CTGCAACAGA TTTCTATGTA TTAATTTTGT ATCCTGCTAC TTTACGGAAT TCACTTATTA     600

GCTTTTTGGT GACATCTTGA GGATTTTCTG AAGAAAATGG CATGGTATGG TAGGACAAGG     660

TGTCATGTCA TCTGCAAACA GTGGCAGTTT TCCTTCTTCC CTTCCAACCT GGATTTCTTT     720

GATTTCTTTC TGTCTGAGTA CGACTAGGAT TCCCAATACT ATACCGAATA AAAGTGGCAA     780

GAGTGGACAT CCTTGTCTTA TTTTTCTGAC CTTAGAGGAA ATGCTTTCAG TTTTTCACCA     840

TTAATTATAA TGTTTACTGT GGGCTTGTCA TATGTGGCCT TCATTATATG GAGGTCTATT     900

CCCTCTATAC CCACCTTGTT GAGAGTTTTT ATCATAAAAG TATGTTGAAT TTGTCAAAA     960
```

```
GTTTTTCCTG CATCTATTGA GATGATTTTT ACTCTTCAAT TCATTAATGA TTTTTATTCT    1020

TCATTTTGTT AATGATTTCC ATTCTTCAAT TTGTTAACGT GGTATATCAC ATTGATTGAT    1080

TTGTGGATAC CTTTGTATCC CTGGGATAAA CCTCACTTGA TCATGAGCTT TCAATGTATT    1140

TTTGAATTCA CTTTGCTAAT ATTCTGTTGG GTATTTTGC ATCTCTATTC ATCAATGATA     1200

TTGGCCTAAG AAAGGTTTTG TCTGGTTTTA GTATCAGGGT GATGCTGGCC TCATAGAGAG    1260

AGTTTAGAAG CATTTCCTCC TCTTTGATTT TTCGGAATAG TTTGAGTAGG ATAGGTATTA    1320

ACTCTTCTTT AAATGTTTGG GGACTTCCCT GGTGAGCCGG TGGTTGAGAA TCCGCCTCAG    1380

GGATGTGGGT TTGATCCCTG GTCAGGGAAC CATTAATAAG ATCCCACATG CTGCAGGCAA    1440

CAAGCCCCCA AGCTGCAACC ACTGAGCTGC AACCGCTGCA GTGCCCACAG GCCACGACCA    1500

GAGAAAGCCC ACATACAGCA GGGAAGACCC AGCACAACCG GAAAAAGGAG TTTGGTGGAA    1560

TACAGCTGTG AAGCCGTCTG GTCCTGGACT CCTGCTTGAG GGAATTTTTT AAAAATTATT    1620

GATTCAATTT CATTACTGGT AACTGGTCTG TTCATATTTT CTATTTCTTC CGGGTTCAGT    1680

CTTGGGAGAT TGTACATGCC TAGGAATGTG TCCGTTTCTT CTAGGTTGTC CATTTTATTG    1740

GACATGCATG GGAGCACACA GCACCGACCA GCGAGACTCA TGCTGGCTTC CTGGGGCCAG    1800

GCTGGGGCCC CAAGCAGCAT GGCATCCTAG AGTGTGTGAA AGCCCACTGA CCCTGCCCAG    1860

CCCCACAATT TCATTCTGAG AAGTGATTCC TTGCTTCTGC ACTTACAGGC CCAGGATCTG    1920

ACCTGCTTCT GAGGAGCAGG GGTTTTGGCA GGACGGGGAG ATGCTGAGAG CCGACGGGGG    1980

TCCAGGTCCC CTCCCAGGCC CCCTGTCTG GGGCAGCCCT TGGGAAAGAT TGCCCCAGTC     2040

TCCCTCCTAC AGTGGTCAGT CCCAGCTGCC CCAGGCCAGA GCTGCTTTAT TTCCGTCTCT    2100

CTCTCTGGAT GGTATTCTCT GGAAGCTGAA GGTTCCTGAA GTTATGAATA GCTTTGCCCT    2160

GAAGGGCATG GTTTGTGGTC ACGGTTCACA GGAACTTGGG AGACCCTGCA GCTCAGACGT    2220

CCCGAGATTG GTGGCACCCA GATTTCCTAA GCTCGCTGGG GAACAGGGCG CTTGTTTCTC    2280

CCTGGCTGAC CTCCCTCCTC CCTGCATCAC CCAGTTCTGA AAGCAGAGCG GTGCTGGGGT    2340

CACAGCCTCT CGCATCTAAC GCCGGTGTCC AAACCACCCG TGCTGGTGTT CGGGGGGCTA    2400

CCTATGGGA AGGGCTTCTC ACTGCAGTGG TGCCCCCCGT CCCCTCTGAG ATCAGAAGTC     2460

CCAGTCCGGA CGTCAAACAG GCCGAGCTCC CTCCAGAGGC TCCAGGGAGG GATCCTTGCC    2520

CCCCCGCTGC TGCCTCCAGC TCCTGGTGCC GCACCCTTGA GCCTGATCTT GTAGACGCCT    2580

CAGTCTAGTC TCTGCCTCCG TGTTCACACG CCTTCTCCCC ATGTCCCCTC CGTGTCCCCG    2640

TTTTCTCTCA CAAGGACACC GGACATTAGA TTAGCCCCTG TTCCAGCCTC ACCTGAACAG    2700

CTCACATCTG TAAAGACCTA GATTCCAAAC AAGATTCCAA CCTGAAGTTC CCGGTGGATG    2760

TGAGTTCTGG GGCGACATCC TTCAACCCCA TCACAGCTTG CAGTTCATCG CAAAACATGG    2820

AACCTGGGGT TTATCGTAAA ACCCAGGTTC TTCATGAAAC ACTGAGCTTC GAGGCTTGTT    2880

GCAAGAATTA AAGGTGCTAA TACAGATCAG GGCAAGGACT GAAGCTGGCT AAGCCTCCTC    2940

TTTCCATCAC AGGAAAGGGG GGCCTGGGGG CGGCTGGAGG TCTGCTCCCG TGAGTGAGCT    3000

CTTTCCTGCT ACAGTCACCA ACAGTCTCTC TGGGAAGGAA ACCAGAGGCC AGAGAGCAAG    3060

CCGGAGCTAG TTTAGGAGAC CCCTGAACCT CCACCCAAGA TGCTGACCAG CCAGCGGGCC    3120

CCCTGGAAAG ACCCTACAGT TCAGGGGGGA AGAGGGGCTG ACCCGCCAGG TCCCTGCTAT    3180

CAGGAGACAT CCCCGCTATC AGGAGATTCC CCCACCTTGC TCCCGTTCCC CTATCCCAAT    3240

ACGCCCACCC CACCCCTGTG ATGAGCAGTT TAGTCACTTA GAATGTCAAC TGAAGGCTTT    3300

TGCATCCCCT TTGCCAGAGG CACAAGGCAC CCACAGCCTG CTGGGTACCG ACGCCCATGT    3360
```

```
-continued

GGATTCAGCC AGGAGGCCTG TCCTGCACCC TCCCTGCTCG GGCCCCCTCT GTGCTCAGCA    3420

ACACACCCAG CACCAGCATT CCCGCTGCTC CTGAGGTCTG CAGGCAGCTC GCTGTAGCCT    3480

GAGCGGTGTG GAGGGAAGTG TCCTGGGAGA TTTAAAATGT GAGAGGCGGG AGGTGGGAGG    3540

TTGGGCCCTG TGGGCCTGCC CATCCCACGT GCCTGCATTA GCCCCAGTGC TGCTCAGCCG    3600

TGCCCCCGCC GCAGGGGTCA GGTCACTTTC CCGTCCTGGG GTTATTATGA CTCTTGTCAT    3660

TGCCATTGCC ATTTTTGCTA CCCTAACTGG GCAGCAGGTG CTTGCAGAGC CCTCGATACC    3720

GACCAGGTCC TCCCTCGGAG CTCGACCTGA ACCCCATGTC ACCCTTGCCC CAGCCTGCAG    3780

AGGGTGGGTG ACTGCAGAGA TCCCTTCACC CAAGGCCACG GTCACATGGT TTGGAGGAGC    3840

TGGTGCCCAA GGCAGAGGCC ACCCTCCAGG ACACACCTGT CCCCAGTGCT GGCTCTGACC    3900

TGTCCTTGTC TAAGAGGCTG ACCCCGGAAG TGTTCCTGGC ACTGGCAGCC AGCCTGGACC    3960

CAGAGTCCAG ACACCCACCT GTGCCCCCGC TTCTGGGGTC TACCAGGAAC CGTCTAGGCC    4020

CAGAGGGGAC TTCCTGCTTG GCCTTGGATG GAAGAAGGCC TCCTATTGTC CTCGTAGAGG    4080

AAGCCACCCC GGGGCCTGAG GATGAGCCAA GTGGGATTCC GGGAACCGCG TGGCTGGGGG    4140

CCCAGCCCGG GCTGGCTGGC CTGCATGCCT CCTGTATAAG GCCCCAAGCC TGCTGTCTCA    4200

GCCCTCCACT CCCTGCAGAG CTCAGAAGCA CGACCCCAGG GATATCATCG ATAAGCTTGG    4260

ATCCCCTGCC GGTGCCTCTG GGGTAAGCTG CCTGCCCTGC CCCACGTCCT GGGCACACAC    4320

ATGGGGTAGG GGGTCTTGGT GGGGCCTGGG ACCCCACATC AGGCCCTGGG GTCCCCCCTG    4380

TGAGAATGGC TGGAAGCTGG GGTCCCTCCT GGCGACTGCA GAGCTGGCTG GCCGCGTGCC    4440

ACTCTTGTGG GTGACCTGTG TCCTGGCCTC ACACACTGAC CTCCTCCAGC TCCTTCCAGC    4500

AGAGCTAAGG CTAAGTGAGC CAGAATGGTA CCTAAGGGGA GGCTAGCGGT CCTTCTCCCG    4560

AGGAGGGGCT GTCCTGGAAC CACCAGCCAT GGAGAGGCTG GCAAGGGTCT GGCAGGTGCC    4620

CCAGGAATCA CAGGGGGGCC CCATGTCCAT TTCAGGGCCC GGGAGCCTTG GACTCCTCTG    4680

GGGACAGACG ACGTCACCAC CGCCCCCCCC CCATCAGGGG GACTAGAAGG GACCAGGACT    4740

GCAGTCACCC TTCCTGGGAC CCAGGCCCCT CCAGGCCCCT CCTGGGGCTC CTGCTCTGGG    4800

CAGCTTCTCC TTCACCAATA AAGGCATAAA CCTGTGCTCT CCCTTCTGAG TCTTTGCTGG    4860

ACGACGGGCA GGGGTGGAG AAGTGGTGGG GAGGGAGTCT GGCTCAGAGG ATGACAGCGG    4920

GGCTGGGATC CAGGGCGTCT GCATCACAGT CTTGTGACAA CTGGGGGCCC ACACACATCA    4980

CTGCGGCTCT TTGAAACTTT CAGGAACCAG GGAGGGACTC GGCAGAGACA TCTGCCAGTT    5040

CACTTGGAGT GTTCAGTCAA CACCCAAACT CGACAAAGGA CAGAAAGTGG AAAATGGCTG    5100

TCTCTTAGTC TAATAAATAT TGATATGAAA CTCAAGTTGC TCATGGATCA ATATGCCTTT    5160

ATGATCCAGC CAGCCACTAC TGTCGTATCA ACTCATGTAC CCAAACGCAC TGATCTGTCT    5220

GGCTAATGAT GAGAGATTCC CAGTAGAGAG CTGGCAAGAG GTCACAGTGA AACTGTCTG    5280

CACACACAGC AGAGTCCACC AGTCATCCTA AGGAGATCAG TCCTGGTGTT CATTGGAGGA    5340

CTGATGTTGA AGCTGAAACT CCAATGCTTT GGCCACCTGA TGTGAAGAGC TGACTCATTT    5400

GAAAAGACCC TGATGCTGGG AAAGATTGAG GGCAGGAGGA GAAGGGGACG ACAGAGGATG    5460

AGATGGTTGG ATGGCATCAC CAACACAATG GACATGGGTT TGGGTGGACT CCAGGAGTTG    5520

GTGATGGACA GGGAGGCCTG GCGTGCTACG GAAGCGGTTT ATGGGGTCAC AAAGACTGAG    5580

TGACTGAACT GAGCTGAACT GAATGGAAAT GAGGTATACA GCAAAGTGGG GATTTTTTAG    5640

ATAATAAGAA TATACACATA ACATAGTGTA TACTCATATT TTTATGCATA CCTGAATGCT    5700

CAGTCACTCA GTCGTATCTG ACTCTGTGAC CTATGGACCG TAGCCTTCCA GGTTTCTTCT    5760
```

-continued

| | | | | | |
|---|---|---|---|---|---|
| GTCCACAGAA | TTCTCCAAGG | CAAGAATACT | GGAGTGGGTA | GCCATTTCCT | CCTCCAGGGG | 5820 |
| ATCCTCCCGA | CCCAGGGATT | GAACCGGCAT | CTCCTGTATT | GGCAGGTGGA | TTCTTTACCA | 5880 |
| CTGTGCCACC | AGGGAAGCCC | GTGTTACTCT | CTATGTCCCA | CTTAATTACC | AAAGCTGCTC | 5940 |
| CAAGAAAAAG | CCCCTGTGCC | CTCTGAGCTT | CCCGGCCTGC | AGAGGGTGGT | GGGGGTAGAC | 6000 |
| TGTGACCTGG | GAACACCCTC | CCGCTTCAGG | ACTCCCGGGC | CACGTGACCC | ACAGTCCTGC | 6060 |
| AGACAGCCGG | GTAGCTCTGC | TCTTCAAGGC | TCATTATCTT | TAAAAAAAAC | TGAGGTCTAT | 6120 |
| TTTGTGACTT | CGCTGCCGTA | ACTTCTGAAC | ATCCAGTGCG | ATGGACAGGA | CCTCCTCCCC | 6180 |
| AGGCCTCAGG | GGCTTCAGGG | AGCCAGCCTT | CACCTATGAG | TCACCAGACA | CTCGGGGGTG | 6240 |
| GCCCCGCCTT | CAGGGTGCTC | ACAGTCTTCC | CATCGTCCTG | ATCAAAGAGC | AAGACCAATG | 6300 |
| ACTTCTTAGG | AGCAAGCAGA | CACCCACAGG | ACACTGAGGT | TCACCAGAGC | TGAGCTGTCC | 6360 |
| TTTTGAACCT | AAAGACACAC | AGCTCTCGAA | GGTTTTCTCT | TTAATCTGGA | TTTAAGGCCT | 6420 |
| ACTTGCCCCT | CAAGAGGGAA | GACAGTCCTG | CATGTCCCCA | GGACAGCCAC | TCGGTGGCAT | 6480 |
| CCGAGGCCAC | TTAGTATTAT | CTGACCGCAC | CCTGGAATTA | ATCGGTCCAA | ACTGGACAAA | 6540 |
| AACCTTGGTG | GGAAGTTTCA | TCCCAGAGGC | CTCAACCATC | CTGCTTTGAC | CACCCTGCAT | 6600 |
| CTTTTTTTCT | TTTATGTGTA | TGCATGTATA | TATATATATA | TATTTTTTTT | TTTTTCATTT | 6660 |
| TTTGGCTGTG | CTGGCTGTTC | GTTGCAGTTC | GGTGCGCAGG | CTTCTCTCTA | GTTTCTCTCT | 6720 |
| AGTCTTCTCT | TATCACAGAG | CAGTCTCTAG | ACGATCGACG | CGT | | 6763 |

(2) INFORMATION FOR SEQ ID NO:24:

(i) SEQUENCE CHARACTERISTICS:
        (A) LENGTH: 5 amino acids
        (B) TYPE: amino acid
        (D) TOPOLOGY: linear (xi) SEQUENCE DESCRIPTION: SEQ ID NO:24:

Arg Ile Arg Lys Arg
1              5

(2) INFORMATION FOR SEQ ID NO:25:

(i) SEQUENCE CHARACTERISTICS:
        (A) LENGTH: 5 amino acids
        (B) TYPE: amino acid
        (D) TOPOLOGY: linear (xi) SEQUENCE DESCRIPTION: SEQ ID NO:25:

Gln Arg Arg Lys Arg
1              5

PROTEIN C PRODUCTION IN NON-HUMAN TRANSGENIC MAMMALS

This application corresponds to U.S. patent application Ser. No. 08/565,074, filed Nov. 30, 1995, which was converted to U.S. Provisional Application No. 60/019,692, filed Jun. 13, 1996, and this application claims benefit of U.S. Provisional Application 60/044,453 filed Nov. 30, 1995.

BACKGROUND OF THE INVENTION

Protein C in its activated form plays an important role in regulating blood coagulation. The activated protein C, a serine protease, inactivates coagulation Factors Va and VIIIa by limited proteolysis. The coagulation cascade initiated by tissue injury, for example, is prevented from proceeding in an unimpeded chain-reaction beyond the area of injury by activated protein C.

Protein C is synthesized in the liver as a single chain precursor polypeptide which is subsequently processed to a light chain of about 155 amino acids ($M_r$=21,000) and a heavy chain of 262 amino acids ($M_r$=40,000). The heavy and light chains circulate in the blood as a two-chain inactive protein, or zymogen, held together by a disulfide bond. When a 12 amino acid residue peptide is cleaved from the amino terminus of the heavy chain portion of the zymogen in a reaction mediated by thrombin, the protein becomes activated. The N-terminal portion of the light chain contains nine γ-carboxyglutamic acid (Gla) residues that are required for the calcium-dependent membrane binding and activation of the molecule. Another blood protein, referred to as "protein S", is believed to accelerate the protein C-catalyzed proteolysis of Factor Va.

Protein C has also been implicated in the action of tissue-type plasminogen activator (Kisiel et al., *Behring Inst. Mitt.* 73:29–42, 1983). Infusion of bovine activated protein C (APC) into dogs results in increased plasminogen activator activity (Comp et al., *J. Clin. Invest.* 68:1221–1228, 1981). Other studies (Sakata et al., *Proc. Natl. Acad. Sci. USA* 82:1121–1125, 1985) have shown that addition of APC to cultured endothelial cells leads to a rapid, dose-dependent increase in fibrinolytic activity in the conditioned media, reflecting increases in the activity of both urokinase-related and tissue-type plasminogen activators. APC treatment also results in a dose-dependent decrease in anti-activator activity. In addition, studies with monoclonal antibodies against endogenous APC (Snow et al., *FASEB Abstracts*, 1988) implicate APC in maintaining patency of arteries during fibrinolysis and limiting the extent of tissue infarct.

Experimental evidence indicates that protein C may be clinically useful in the treatment of thrombosis. Several studies with baboon models of thrombosis have indicated that activated protein C in low doses will be effective in prevention of fibrin deposition, platelet deposition and loss of circulation (Gruber et al., *Hemostasis and Thrombosis* 374a: abstract 1512, 1988; Widrow et al., *Fibrinolysis* 2 suppl. 1: abstract 7, 1988; Griffin et al., *Thromb. Haemostasis* 62: abstract 1512, 1989).

In addition, exogenous activated protein C has been shown to prevent the coagulopathic and lethal effects of gram negative septicemia (Taylor et al., *J. Clin. Invest.* 19:918–925, 1987). Data obtained from studies with baboons suggest that activated protein C plays a natural role in protecting against septicemia.

Until recently, protein C was purified from clotting factor concentrates (Marlar et al., *Blood* 59:1067–1072, 1982) or from plasma (Kisiel, *J. Clin. Invest.* 64:761–769, 1979) and activated in vitro. However, the possibility that the resulting product could be contaminated with such infectious agents as hepatitis virus, cytomegalovirus, or human immunodeficiency virus (HIV) make the process unfavorable.

While expression of protein C through recombinant means has been theoretically possible as the genes for both human and bovine protein C are known (Foster et al., *Proc. Natl. Acad. Sci. USA* 82:4673–4677, 1985; Foster et al., *Proc. Natl. Acad Sci. USA* 81:4766–4770, 1984 and U.S. Pat. No. 4,775,624), it has been met with limited success. Expression of some vitamin K-dependent proteins, such as protein C in cultured cells, has not produced protein C that has been at both commercially valuable levels and biologically functional when activated (i.e. had anticoagulant activity (Grinnell et al., in Bruley and Drohn, eds., *Protein C and Related Anticoagulants:*29–63, Gulf Publishing, Houston, Tex. and Grinnell et al., *Bio/Technol.* 5:1189–1192, 1987)). Transgenic expression of protein C has yielded somewhat higher levels of expression, but the recombinant protein's anticoagulant activity has still remained low, with less than 50% of the material having biological activity (Velander et al., *Proc. Natl. Acad. Sci. USA* 89:12003–12007, 1992). Therefore, there remains a need for producing protein C that is both expressed at high levels and has therapeutic value.

SUMMARY OF THE INVENTION

It is an object of the present invention to provide methods for producing protein C in transgenic animals. It is a further object to provide transgenic animals that express human protein C in a mammary gland.

Within one aspect, the present invention provides methods for producing protein C in a transgenic animal comprising (a) providing a DNA construct comprising a first DNA segment encoding a secretion signal and a protein C propeptide operably linked to a second DNA segment encoding protein C, wherein the encoded protein C comprises a two-chain cleavage site modified from Lys-Arg to $R_1$-$R_2$-$R_3$-$R_4$, and wherein each of $R_1$–$R_4$ is individually Lys or Arg, and wherein said first and second segments are operably linked to additional DNA segments required for expression of the protein C DNA in a lactating mammary gland of a host female animal; (b) introducing said DNA construct into a fertilized egg of a non-human mammalian species; (c) inserting said egg into an oviduct or uterus of a female of said species to obtain offspring carrying said DNA construct; (d) breeding said offspring to produce female progeny that express said first and second DNA segments and produce milk containing protein C encoded by said second segment, wherein said protein has anticoagulant activity upon activation; (e) collecting milk from said female progeny; and (f) recovering the protein C from the milk. In one embodiment, $R_1$-$R_2$-$R_3$-$R_4$ is Arg-Arg-Lys-Arg (SEQ ID NO: 20). In another embodiment, the method further comprises the step of activating the protein C. In another embodiment, the non-human mammalian species is selected from sheep, rabbits, cattle and goats. In another embodiment each of the first and second DNA segments comprises an intron. In another embodiment, the second DNA segment comprises a DNA sequence of nucleotides as shown in SEQ ID NO: 1 or SEQ ID NO:3. In another embodiment, the additional DNA segments comprise a transcriptional promoter selected from the group consisting of casein, β-lactoglobulin, α-lactoglobulin, α-lactalbumin and whey acidic protein gene promoters.

In another aspect, the present invention provides a transgenic non-human female mammal that produces recoverable amounts of human protein C in its milk, wherein at least 90% of the human protein C in the milk is two-chain protein C.

In another aspect, the present invention provides a process for producing a transgenic offspring of a mammal comprising the steps of (a) providing a DNA construct comprising a first DNA segment encoding a secretion signal and a protein C propeptide operably linked to a second DNA segment encoding protein C, wherein the encoded protein C comprises a two-chain cleavage site modified from Lys-Arg to $R_1$-$R_2$-$R_3$-$R_4$, and wherein each of $R_1$–$R_4$ is individually Lys or Arg, and wherein said first and second segments are operably linked to additional DNA segments required for expression of the protein C DNA in a lactating mammary gland of a host female animal; (b) introducing said DNA construct into a fertilized egg of a non-human mammalian species; and (c) inserting said egg into an oviduct or uterus of a female of said species to obtain offspring carrying said DNA construct.

Within another aspect, the present invention provides non-human mammals produced according to the process for producing a transgenic offspring of a mammal comprising the steps of (a) providing a DNA construct comprising a first DNA segment encoding a secretion signal and a protein C propeptide operably linked to a second DNA segment encoding protein C, wherein the encoded protein C comprises a two-chain cleavage site modified from Lys-Arg to $R_1$-$R_2$-$R_3$-$R_4$, and wherein each of $R_1$–$R_4$ is individually Lys or Arg, and wherein said first and second segments are operably linked to additional DNA segments required for expression of the protein C DNA in a lactating mammary gland of a host female animal; (b) introducing said DNA construct into a fertilized egg of a non-human mammalian species; and (c) inserting said egg into an oviduct or uterus of a female of said species to obtain offspring carrying said DNA construct.

In another aspect, the present invention provides a non-human mammalian embryo containing in its nucleus a heterologous DNA segment encoding protein C, wherein the encoded protein C comprises a two-chain cleavage site modified from Lys-Arg to $R_1$-$R_2$-$R_3$-$R_4$, and wherein each of $R_1$–$R_4$ is individually Lys or Arg.

DETAILED DESCRIPTION OF THE INVENTION

Figure 1:
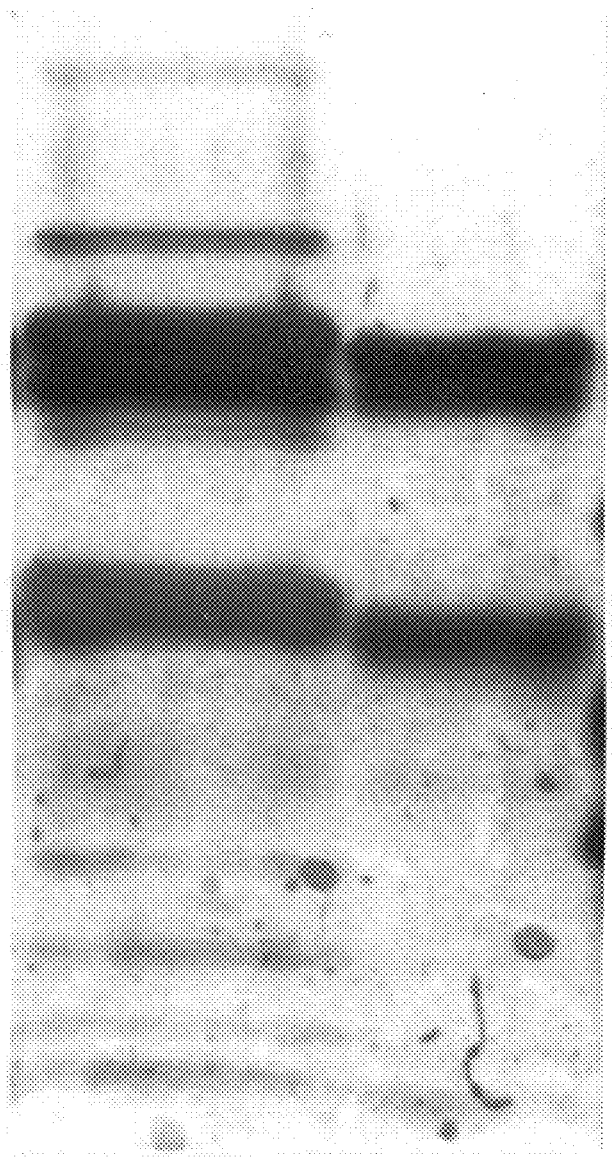
FIG. 1 illustrates analysis of plasma-derived and transgenic protein C run under non-reducing and reducing conditions. Lane 1 is plasma-derived protein C and lane 2 is transgenic protein C from the milk of sheep 30851.

Prior to setting forth the invention in detail, it will be helpful to define certain terms used herein:

As used herein, the term "biologically active" is used to denote protein C that is characterized by its anticoagulant and fibrinolytic properties. Protein C, when activated, inactivates factor Va and factor VIIIa in the presence of phospholipid and calcium. Activated protein C also enhances fibrinolysis, an effect believed to be mediated by the lowering of the levels of plasminogen activator inhibitors. As stated previously, two-chain protein C is activated upon cleavage of a 12 amino acid peptide from the amino terminus of the heavy chain portion of the zymogen.

The term "egg" is used to denote an unfertilized ovum, a fertilized ovum prior to fusion of the pronuclei or an early stage embryo (fertilized ovum with fused pronuclei).

A "female mammal that produces milk containing biologically active protein C" is one that, following pregnancy and delivery, produces, during the lactation period, milk containing recoverable amounts of protein C that can be activated to be biologically active. Those skilled in the art will recognized that such animals will naturally produce milk, and therefore the protein C, discontinuously.

The term "progeny" is used in its usual sense to include offspring and descendants.

The term "heterologous" is used to denote genetic material originating from a different species than that into which it has been introduced, or a protein produced from such genetic material.

Within the present invention, transgenic animal technology is employed to produce protein C within a mammary gland of a host female mammal. Expression in the mammary gland and subsequent secretion of the protein of interest into the milk overcomes many difficulties encountered in isolating proteins from other sources. Milk is readily collected, available in large quantities, and well characterized biochemically. Furthermore, the major milk proteins are present in milk at high concentrations (from about 1 to 16 g/l).

From a commercial point of view, it is clearly preferable to use as the host a species that has a large milk yield. While smaller animals such as mice and rats can be used (and are preferred at the proof-of-concept stage), within the present invention it is preferred to use livestock mammals including sheep and cattle. Sheep are particularly preferred due to such factors as the previous history of transgenesis in this species, milk yield, generation time, cost and the ready availability of equipment for collecting sheep milk. It is generally desirable to select a breed of host animal that has been bred for dairy use, such as East Friesland sheep, or to introduce dairy stock by breeding of the transgenic line at a later date. In any event, animals of known, good health status should be used.

Cloned DNA sequences encoding human protein C have been described (Foster and Davie, *Proc. Natl. Acad. Sci. USA* 81:4766–4770, 1984; Foster et al., *Proc. Natl. Acad. USA* 82:4673–4677, 1985; and Bang et al., U.S. Pat. No. 4,755,624, each incorporated herein by reference). Complementary cDNAs encoding protein C can be obtained from libraries prepared from liver cells of various mammalian species according to standard laboratory procedures. DNAs from other species, such as the protein C encoded by rats, pigs, sheep, cows and primates can be used and can be identified using probes from human cDNA.

In a preferred embodiment, human genomic DNAs encoding protein C are used. The human protein C gene is composed of nine exons ranging in size from 25 to 885 nucleotides, and seven introns ranging in size from 92 to 2668 nucleotides (U.S. Pat. No. 4,959,318, incorporated herein by reference). The first exon is non-coding and referred to as exon O. Exon I and a portion of exon II code for the 42 amino acid signal sequence and propeptide (i.e., pre-propeptide). The remaining portion of exon II, exon III, exon IV, exon V and a portion of exon VI code for the light chain of protein C. The remaining portion of exon VI, exon VII and exon VIII code for the heavy chain of protein C. A representative human genomic DNA sequence and corresponding amino acid sequence are shown in SEQ ID NOS:

1 and 2, respectively. A representative human protein C cDNA sequence and corresponding amino acid sequences are shown in SEQ ID NO: 3 and 4, respectively.

Those skilled in the art will recognize that naturally occurring allelic variants of these sequences will exist; that additional variants can be generated by amino acid substitution, deletion, or insertion; and that such variants are useful within the present invention. In general, it is preferred that any engineered variants comprise only a limited number of amino acid substitutions, deletions, or insertions, and that any substitutions are conservative. Thus, it is preferred to produce protein C polypeptides that are at least 90%, and more preferably at least 95% or more identical in sequence to the corresponding native protein.

Within the present invention, the proteolytic processing involved in the maturation of recombinant protein C from single chain form to the two-chain form (i.e., cleaved between the light chain and the heavy chain) has been enhanced by modifying the amino acid sequence around the two-chain cleavage site. In the normal situation, endoproteolytic cleavage of the precursor molecule at the $Arg_{157}$-$Asp_{158}$ bond and the removal of the dipeptide $Lys_{156}$-$Arg_{157}$ by a carboxypeptidase activity generate the light and heavy chains of protein C prior to secretion. Expression of protein C with the native (Lys-Arg) two-chain cleavage site produces protein C that may contain up to 40% or more uncleaved, single-chain protein C (Grinnel et al., in Protein C and Related Anticoagulants, eds., Bruley and Drohan, Gulf, Houston, pp. 29–63, 1990; Suttie, *Thromb. Res.* 44:129–134, 1986 and Yan et al., *Trends Biochem. Sci.* 14:264–268, 1989). The single-chain form of protein C may not be able to be activated. The cleavage site may be in the form of the amino acid sequence $R_1$-$R_2$-$R_3$-$R_4$, wherein each of R1 through R4 is individually lysine (Lys) or arginine (Arg). Particularly preferred sequences include Arg-Arg-Lys-Arg (SEQ ID NO: 20) and Lys-Arg-Lys-Arg (SEQ ID NO: 21).

In a preferred embodiment, the present invention provides for recoverable amounts of human protein C in the milk of a non-human mammal, where at least 90%, preferably at least 95%, of the human protein C is two-chain protein C.

To obtain expression in the mammary gland, a transcription promoter from a milk protein gene is used. Milk protein genes include those genes encoding caseins, beta-lactoglobulin (BLG), α-lactalbumin, and whey acidic protein. The beta-lactoglobulin promoter is preferred. In the case of the ovine beta-lactoglobulin gene, a region of at least the proximal 406 bp of 5' flanking sequence of the ovine BLG gene (contained within nucleotides 3844 to 4257 of SEQ ID NO: 5) will generally be used. Larger portions of the 5' flanking sequence, up to about 5 kb, are preferred. A larger DNA segment encompassing the 5' flanking promoter region and the region encoding the 5' non-coding portion of the beta-lactoglobulin gene (contained within nucleotides 1 to 4257 of SEQ ID NO: 5) is particularly preferred. See Whitelaw et al., *Biochem J.* 286: 31–39, 1992. Similar fragments of promoter DNA from other species are also suitable.

Other regions of the beta-lactoglobulin gene may also be incorporated in constructs, as may genomic regions of the gene to be expressed. It is generally accepted in the art that constructs lacking introns, for example, express poorly in the transgenic lactating mammary gland in comparison with those constructs that contain introns (see Brinster et al., *Proc. Natl. Acad. Sci. USA* 85: 836–840, 1988; Palmiter et al., *Proc. Natl. Acad. Sci. USA* 88: 478–482, 1991; Whitelaw et al., *Transgenic Res.* 1: 3–13, 1991; WO 89/01343; WO 91/02318). In this regard, it is generally preferred, where possible, to use genomic sequences containing all or some of the native introns of a gene encoding protein C. Within certain embodiments of the invention, the further inclusion of at least some introns from the beta-lactoglobulin gene is preferred. One such region is a DNA segment which provides for intron splicing and RNA polyadenylation from the 3' non-coding region of the ovine beta-lactoglobulin gene. When substituted for the natural 3' non-coding sequences of a gene, this ovine beta-lactoglobulin segment can both enhance and stabilize expression levels of the protein C.

For expression of protein C, DNA segments encoding protein C are operably linked to additional DNA segments required for their expression to produce expression units. One such additional segment is the above-mentioned milk protein gene promoter. Sequences allowing for termination of transcription and polyadenylation of mRNA may also be incorporated. Such sequences are well known in the art, for example, one such termination sequence is the "upstream mouse sequence" (McGeady et al., *DNA* 5:289–298,1986). The expression units will further include a DNA segment encoding a secretion signal operably linked to the segment encoding the protein C polypeptide chain The secretion signal may be a native protein C secretion signal or may be that of another protein, such as a milk protein. The term "secretion signal" is used herein to denote that portion of a protein that directs it through the secretory pathway of a cell to the outside. Secretion signals are most commonly found at the amino termini of proteins. See, for example, von Heinje, *Nuc. Acids Res.* 14: 4683–4690, 1986; and Meade et al., U.S. Pat. No. 4,873,316, which are incorporated herein by reference.

Construction of expression units is conveniently carried out by inserting a protein C sequence into a plasmid or phage vector containing the additional DNA segments, although the expression unit may be constructed by essentially any sequence of ligations. It is particularly convenient to provide a vector containing a DNA segment encoding a milk protein and to replace the coding sequence for the milk protein with that of a protein C (including a secretion signal), thereby creating a gene fusion that includes the expression control sequences of the milk protein gene. In any event, cloning of the expression units in plasmids or other vectors facilitates the amplification of the protein C sequences. Amplification is conveniently carried out in bacterial (e.g. *E. coli*) host cells, thus the vectors will typically include an origin of replication and a selectable marker functional in bacterial host cells.

The expression unit is then introduced into fertilized eggs (including early-stage embryos) of the chosen host species. Introduction of heterologous DNA can be accomplished by one of several routes, including pronuclear microinjection (e.g. U.S. Pat. No. 4,873,191), retroviral infection (Jaenisch, *Science* 240: 1468–1474, 1988) or site-directed integration using embryonic stem (ES) cells (reviewed by Bradley et al., *Bio/Technology* 10: 534–539, 1992). The eggs are then implanted into the oviducts or uteri of pseudopregnant females and allowed to develop to term. Offspring carrying the introduced DNA in their germ line can pass the DNA on to their progeny in the normal, Mendelian fashion, allowing the development of transgenic herds. General procedures for producing transgenic animals are known in the art. See, for example, Hogan et al., *Manipulating the Mouse Embryo: A Laboratory Manual*, Cold Spring Harbor Laboratory, 1986; Simons et al., *Bio/Technology* 6: 179–183, 1988; Wall et al., *Biol. Reprod.* 32: 645–651, 1985; Buhler et al., *Bio/*

Technology 8: 140–143, 1990; Ebert et al., Bio/Technology 9: 835–838, 1991; Krimpenfort et al., Bio/Technology 9: 844–847, 1991; Wall et al., J. Cell, Biochem. 49: 113–120, 1992; and WIPO publications WO 88/00239, WO 90/05188, WO 92/11757; and GB 87/00458, which are incorporated herein by reference. Techniques for introducing foreign DNA sequences into mammals and their germ cells were originally developed in the mouse. See, e.g., Gordon et al., Proc. Natl. Acad. Sci. USA 77: 7380–7384, 1980; Gordon and Ruddle, Science 214: 1244–1246, 1981; Palmiter and Brinster, Cell 41: 343–345, 1985; Brinster et al., Proc. Natl. Acad. Sci. USA 82: 4438–4442, 1985; and Hogan et al. (ibid.). These techniques were subsequently adapted for use with larger animals, including livestock species (see e.g., WIPO publications WO 88/00239, WO 90/05188, and WO 92/11757; and Simons et al., Bio/Technology 6: 179–183, 1988). To summarize, in the most efficient route used to date in the generation of transgenic mice or livestock, several hundred linear molecules of the DNA of interest are injected into one of the pro-nuclei of a fertilized egg. Injection of DNA into the cytoplasm of a zygote can also be employed.

In general, female animals are superovulated by treatment with follicle stimulating hormone, then mated. Fertilized eggs are collected, and the heterologous DNA is injected into the eggs using known methods. See, for example, U.S. Pat. No. 4,873,191; Gordon et al., Proc. Natl. Acad. Sci. USA 82: 7380–7384, 1980; Gordon and Ruddle, Science 214: 1244–1246, 1981; Palmiter and Brinster, Cell 41: 343–345, 1985; Brinster et al., Proc. Natl. Acad, Sci. USA 82: 4438–4442, 1985; Hogan et al., Manipulating the Mouse Embryo: A Laboratory Manual, Cold Spring Harbor Laboratory, 1986; Simons et al. Bio/Technology 6: 179–183, 1988; Wall et al., Biol. Reprod. 32: 645–651, 1985; Buhler et al., Bio/Technology 8: 140–143, 1990; Ebert et al., Bio/Technology 9: 835–838, 1991; Krimpenfort et al., Bio/Technology 9: 844–847, 1991; Wall et al., J. Cell. Biochem. 49: 113–120, 1992; WIPO publications WO 88/00239, WO 90/05118, and WO 92/11757; and GB 87/00458, which are incorporated herein by reference.

For injection into fertilized eggs, the expression units are removed from their respective vectors by digestion with appropriate restriction enzymes. For convenience, it is preferred to design the vectors so that the expression units are removed by cleavage with enzymes that do not cut either within the expression units or elsewhere in the vectors. The expression units are recovered by conventional methods, such as electro-elution followed by phenol extraction and ethanol precipitation, sucrose density gradient centrifugation, or combinations of these approaches.

DNA is injected into eggs essentially as described in Hogan et al., ibid. In a typical injection, eggs in a dish of an embryo culture medium are located using a stereo zoom microscope (×50 or ×63 magnification preferred). Suitable media include Hepes (N-2-hydroxyethylpiperazine-N'-2-ethanesulphonic acid) or bicarbonate buffered media such as M2 or M16 (available from Sigma Chemical Co., St. Louis, USA) or synthetic oviduct medium (disclosed below). The eggs are secured and transferred to the center of a glass slide on an injection rig using, for example, a drummond pipette complete with capillary tube. Viewing at lower (e.g. ×4) magnification is used at this stage. Using the holding pipette of the injection rig, the eggs are positioned centrally on the slide. Individual eggs are sequentially secured to the holding pipette for injection. For each injection process, the holding pipette/egg is positioned in the center of the viewing field. The injection needle is then positioned directly below the egg. Preferably using ×40 Nomarski objectives, both manipulator heights are adjusted to focus both the egg and the needle. The pronuclei are located by rotating the egg and adjusting the holding pipette assembly as necessary. Once the pronucleus has been located, the height of the manipulator is altered to focus the pronuclear membrane. The injection needle is positioned below the egg such that the needle tip is in a position below the center of the pronucleus. The position of the needle is then altered using the injection manipulator assembly to bring the needle and the pronucleus into the same focal plane. The needle is moved, via the joy stick on the injection manipulator assembly, to a position to the right of the egg. With a short, continuous jabbing movement, the pronuclear membrane is pierced to leave the needle tip inside the pronucleus. Pressure is applied to the injection needle via, for example, a glass syringe until the pronucleus swells to approximately twice its volume. At this point, the needle is slowly removed. Reverting to lower (e.g. ×4) magnification, the injected egg is moved to a different area of the slide, and the process is repeated with another egg.

After the DNA is injected, the eggs may be cultured to allow the pronuclei to fuse, producing one-cell or later stage embryos. In general, the eggs are cultured at approximately the body temperature of the species used in a buffered medium containing balanced salts and serum. Surviving embryos are then transferred to pseudopregnant recipient females, typically by inserting them into the oviduct or uterus, and allowed to develop to term. During embryogenesis, some of the injected DNA integrates in a random fashion in the genomes of a small number of the developing embryos.

Potential transgenic offspring are screened via blood samples and/or tissue biopsies. DNA is prepared from these samples and examined for the presence of the injected construct by techniques such as polymerase chain reaction (PCR; see Mullis, U.S. Pat. No. 4,683,202) and Southern blotting (Southern, J. Mol. Biol. 98:503, 1975; Maniatis et al., Molecular Cloning: A Laboratory Manual, Cold Spring Harbor Laboratory, 1982). Founder transgenic animals, or G0s, may be wholly transgenic, having transgenes in all of their cells, or mosaic, having transgenes in only a subset of cells (see, for example, Wilkie et al., Develop. Biol. 118: 9–18, 1986). In the latter case, groups of germ cells may be wholly or partially transgenic. In the latter case, the number of transgenic progeny from a founder animal will be less than the expected 50% predicted from Mendelian principles. Founder G0 animals are grown to sexual maturity and mated to obtain offspring, or G1s. The G1s are also examined for the presence of the transgene to demonstrate transmission from founder G0 animals. In the case of male G0s, these may be mated with several non-transgenic females to generate many offspring. This increases the chances of observing transgene transmission. Female G0 founders may be mated naturally, artificially inseminated or superovulated to obtain many eggs which are transferred to surrogate mothers. The latter course gives the best chance of observing transmission in animals having a limited number of young. The above-described breeding procedures are used to obtain animals that can pass the DNA on to subsequent generations of offspring in the normal, Mendelian fashion, allowing the development of, for example, colonies (mice), flocks (sheep), or herds (pigs, goats and cattle) of transgenic animals.

The milk from lactating G0 and G1 females is examined for the expression of the heterologous protein using immunological techniques such as ELISA (see Harlow and Lane, Antibodies, A Laboratory Manual, Cold Spring Harbor Laboratory, 1988) and Western blotting (Towbin et al., *Proc. Natl. Acad. Sci. USA* 76: 4350–4354, 1979). For a variety of reasons known in the art, expression levels of the heterologous protein will be expected to differ between individuals.

A satisfactory family of animals should satisfy three criteria: they should be derived from the same founder G0 animal; they should exhibit stable transmission of the transgene; and they should exhibit acceptably stable expression levels from generation to generation and from lactation to lactation of individual animals. These principles have been demonstrated and discussed (Carver et al., *Bio/Technology* 11: 1263–1270, 1993). Animals from such a suitable family are referred to as a "line." Initially, male animals, G0 or G1, are used to derive a flock or herd of producer animals by natural or artificial insemination. In this way, many female animals containing the same transgene integration event can be quickly generated from which a supply of milk can be obtained.

The protein C is recovered from milk using standard practices such as skimming, precipitation, filtration and protein chromatography techniques.

Protein C produced according to the present invention can be activated by removal of the activation peptide from the amino terminus of the heavy chain. Activation can be achieved using methods that are well known in the art, for example, using α-thrombin (Marlar et al., *Blood* 59:1067–1072, 1982), trypsin (Marlar et al., 1982, ibid.), Russel's viper venom factor X activator (Kisiel, *J. Clin. Invest.* 64:761–769, 1979) or commercially available Protac C (American Diagnostica, NY, N.Y.).

The protein C molecules provided by the present invention and pharmaceutical compositions thereof are particularly useful for administration to humans to treat a variety of conditions involving intravascular coagulation. For instance, although deep vein thrombosis and pulmonary embolism can be treated with conventional anticoagulants, the activated protein C described herein may be used to prevent the occurrence of thromboembolic complications in identified high risk patients, such as those undergoing surgery or those with congestive heart failure. Since activated protein C is more selective than heparin, being active in the body generally when and where thrombin is generated and fibrin thrombi are formed, activated protein C will be more effective and less likely to cause bleeding complications than heparin when used prophylactically for the prevention of deep vein thrombosis. The dose of activated protein C for prevention of deep vein thrombosis is in the range of about 100 μg to 100 mg/day, and administration should begin at least about 6 hours prior to surgery and continue at least until the patient becomes ambulatory. In established deep vein thrombosis and/or pulmonary embolism, the dose of activated protein C ranges from about 100 μg to 100 mg as a loading dose followed by maintenance doses ranging from 3 to 300 mg/day. Because of the lower likelihood of bleeding complications from activated protein C infusions, activated protein C can replace or lower the dose of heparin during or after surgery in conjunction with thrombectomies or embolectomies.

The activated protein C compositions of the present invention will also have substantial utility in the prevention of cardiogenic emboli and in the treatment of thrombotic strokes. Because of its low potential for causing bleeding complications and its selectivity, activated protein C can be given to stroke victims and may prevent the extension of the occluding arterial thrombus. The amount of activated protein C administered will vary with each patient depending on the nature and severity of the stroke, but doses will generally be in the range of those suggested below.

Pharmaceutical compositions of activated protein C provided herein will be a useful treatment in acute myocardial infarction because of the ability of activated protein C to enhance in vitro fibrinolysis. Activated protein C can be given with tissue plasminogen activator or streptokinase during the acute phases of the myocardial infarction. After the occluding coronary thrombus is dissolved, activated protein C can be given for subsequent days or weeks to prevent coronary reocculsion. In acute myocardial infarction, the patient is given a loading dose of at least about 1–500 mg of activated protein C, followed by maintenance doses of 1–100 mg/day.

Activated protein C is useful in the treatment of disseminated intravascular coagulation (DIC). Patients with DIC characteristically have widespread microcirculatory thrombi and often severe bleeding problems which result from consumption of essential clotting factors. Because of its selectivity, activated protein C will not aggravate the bleeding problems associated with DIC, as do conventional anticoagulants, but will retard or inhibit the formation of additional microvascular fibrin deposits.

The invention is further illustrated by the following non-limiting examples.

EXAMPLES

Example I

A. Vector pMAD6 Construction

The multiple cloning site of the vector pUC18 (Yanisch-Perron et al., *Gene* 33:103–119, 1985) was removed and replaced with a synthetic double stranded oligonucleotide (the strands of which are shown in SEQ ID NO: 6 and SEQ ID NO: 7) containing the restriction sites Pvu I/Mlu I/Eco RV/Xba I/Pvu I/Mlu I, and flanked by 5' overhangs compatible with the restriction sites Eco RI and Hind III. pUC18 was cleaved with both Eco RI and Hind III, the 5' terminal phosphate groups were removed with calf intestinal phosphatase, and the oligonucleotide was ligated into the vector backbone. The DNA sequence across the junction was confirmed by sequencing, and the new plasmid was called pUCPM.

The β-lactoglobulin (BLG) gene sequences from pSS1tgXS (disclosed in WIPO publication WO 88/00239) were excised as a Sal I-Xba I fragment and recloned into the vector pUCPM that had been cut with Sal I and Xba I to construct vector pUCXS. pUCXS is thus a pUC18 derivative containing the entire BLG gene from the Sal I site to the Xba I site of phage SS1 (Ali and Clark, *J. Mol. Biol.* 199: 415–426, 1988).

The plasmid pSS1tgSE (disclosed in WIPO publication WO 88/00239) contains a 1290 bp BLG fragment flanked by Sph I and EcoR I restriction sites, a region spanning a unique Not I site and a single Pvu II site which lies in the 5' untranslated leader of the BLG mRNA. Into this Pvu II site was ligated a double stranded, 8 bp DNA linker (5'-GGATATCC-3') encoding the recognition site for the enzyme Eco RV. This plasmid was called pSS1tgSE/RV. DNA sequences bounded by Sph I and Not I restriction sites in pSS1tgSE/RV were excised by enzymatic digestion and used to replace the equivalent fragment in pUCXS. The resulting plasmid was called pUCXSRV. The sequence of the BLG insert in pUCXSRV is shown in SEQ ID NO: 5, with the unique Eco RV site at nucleotide 4245 in the 5' untranslated leader region of the BLG gene. This site allows insertion of any additional DNA sequences under the control of the BLG promoter 3' to the transcription initiation site.

Using the primers BLGAMP3 (5'-TGG ATC CCC TGC CGG TGC CTC TGG-3'; SEQ ID NO: 8) and BLGAMP4 (5'-AAC GCG TCA TCC TCT GTG AGC CAG-3'; SEQ ID NO: 9) a PCR fragment of approximately 650 bp was produced from sequences immediately 3' to the stop codon of the BLG gene in pUCXSRV. The PCR fragment was engineered to have a BamH I site at its 5' end and an Mlu I site at its 3' end and was cloned as such into BamH I and Mlu I cut pGEM7zf(+) (Promega) to give pDAM200(+).

pUCXSRV was digested with Kpn I, and the largest, vector containing band was gel purified. This band contained the entire pUC plasmid sequences and some 3' non-coding sequences from the BLG gene. Into this backbone was ligated the small Kpn I fragment from pDAM200(+) which, in the correct orientation, effectively engineered a Bam HI site at the extreme 5' end of the 2.6 Kbp of the BLG 3' flanking region. This plasmid was called pBLAC200. A 2.6 Kbp Cla I-Xba I fragment from pBLAC200 was ligated into Cla I-Xba I cut pSP72 vector (Promega), thus placing an Eco RV site immediately upstream of the BLG sequences. This plasmid was called pBLAC210.

The 2.6 Kbp Eco RV-Xba I fragment from pBLAC210 was ligated into Eco RV-Xba I cut pUCXSRV to form pMAD6 (SEQ ID NO: 23). This, in effect, excised all coding and intron sequences from pUCXSRV, forming a BLG minigene consisting of 4.2 Kbp of 5' promoter and 2.6 Kbp of 3' downstream sequences flanking a unique Eco RV site. An oligonucleotide linker (ZC6839: ACTACGTAGT; SEQ ID NO: 10) was inserted into the Eco RV site of pMAD6 (SEQ ID NO: 23). This modification destroyed the Eco RV site and created a Sna BI site to be used for cloning purposes. The vector was designated pMAD6-Sna. Messenger RNA initiates upstream of the Sna BI site and terminates downstream of the Sna BI site. The precursor transcript will encode a single BLG-derived intron, intron 6, which is entirely within the 3' untranslated region of the gene.

B. Intronless Vector pMAD

The beta-lactoglobulin cloning vector pMAD was also constructed to allow the insertion of cDNAs under the control of the beta-lactoglobulin gene promoter in constructs containing no introns. To generate pMAD, the plasmid pBLAC100 was opened by digestion with both Eco RV and Sal I. The vector fragment was gel purified and the linearized vector was ligated with the 4.2 kb promoter fragment from the plasmid pUCXSRV as a Sal I-Eco RV fragment. The resulting construct was designated pST1 and constitutes a beta-lactoglobulin mini-gene encompassing a 4.2 kb of promoter region and 2.1 kb of 3' non-coding region beginning immediately downstream of the beta-lactoglobuling translational termination codon. A unique Eco RV site allows blunt-end cloning of any additional DNA sequences. To generate transgenic animals it is generally accepted in the art and preferred to separate bacterial plasmid vector sequences from those intended to be used in the generation of transgenic animals. In order to allow the practical excision of novel cDNA based constructs using this beta-lactoglobulin mini-gene, the minigene was excised from pST1 on a Xho I-Not I fragment, the DNA termini made flush with Klenow polymerase and the product was ligated into the Eco RV site of pUCPM to yield pMAD. Digestion with Mlu I liberates beta-lactoglobulin-cDNA constructs from the bacterial vector backbone.

Intronless constructs based on cDNAs and vectors such as pMAD benefit from the use of "rescue technology" for efficient expression. Rescue technology takes advantage of the ability of a co-injected and co-integrated BLG gene to improve the expression levels obtained from intronless, cDNA-based constructs in the transgenic system. Rescue technology is disclosed in WIPO publication WO 92/11358, and is incorporated herein by reference.

Example 2

A. Isolation of cDNA

A cDNA sequence coding for human protein C was prepared as described in U.S. Pat. No. 4,959,318, which is incorporated herein by reference. Briefly, a genomic fragment containing an exon corresponding to amino acids −42 to −19 (SEQ ID NO: 1) of the pre-pro peptide of protein C was isolated, nick translated and used as a probe to screen a cDNA library constructed by the technique of Gubler and Hoffman, Gene 25:263–269, 1983, using mRNA from HepG2 cells. This cell line was derived from human hepatocytes and was previously shown to synthesize protein C (Fair and Bahnak, Blood 64:194–204, 1984). Positive clones comprising cDNA inserted into the Eco RI site of phage λgtll were isolated and screened with an oligonucleotide probe corresponding to the 5' non-coding region of the protein C gene. One clone was also positive with this probe and its entire nucleotide sequence was determined. The cDNA contained 70 bp of 5' untranslated sequence, the entire coding sequence for human prepro-protein C, and the entire 3' non-coding region corresponding to the second polyadenylation site.

B. Subcloning of Protein C cDNA

The vector pDX was derived from pD3, which was generated from plasmid pDHFRIII (Berkner et al., Nuc. Acids Res. 13:841–857, 1985). The Pst I site immediately upstream from the DHFR sequence in pDHFRIII was converted to a Bcl I site by digestion with Pst I. The DNA was phenol extracted, ethanol precipitated and resuspended in buffer B (50 mM Tris pH 8, 7 mM MgCl$_2$, 7 mM β-MSH). A ligation reaction containing the linearized plasmid DNA and Bcl I linkers was done. The resulting plasmid was phenol extracted, ethanol precipitated and digested with Bcl I and gel purified. The gel purified plasmid DNA was circularized by ligation and used to transform E. coli HB101. Positive colonies were identified by restriction analysis and designated PDHFR'. DNA from positive colonies was isolated and used to transform dam$^-$ E. coli.

Plasmid pD2' was generated by cleaving pDHFR' and pSV40 (comprising Bam HI digested SV40 DNA cloned into the Bam HI site of pML-1 (Lusky et al., Nature 293:79–81, 1981)) with Bcl I and Bam HI. The DNA fragments were resolved by gel electrophoresis, and the 4.9 kb pDHFR' fragment and 0.2 kb SV40 fragment were isolated. These fragments were used in a ligation reaction, and the resulting plasmid, designated pD2', was used to transform E. coli RRI.

Plasmid pD2' was modified by deleting the "poison" sequences in the pBR322 region (Lusky et al., 1981, ibid.). Plasmids pD2' and pML-1 were digested with Eco RI and Nru I. The 1.7 kb pD2' fragment and 1.8 kb pML-1 fragment were isolated by gel purification, circularized in a ligation reaction and used to transform E. coli HB101. Positive colonies were identified using restriction analysis (designated pD2) and digested with Eco RI and Bcl I. A 2.8 kb fragment (fragment C) was isolated and gel purified.

To generate the remaining fragments used in constructing pD3, pDHFRIII was modified to convert the Sac II (Sst II) site into either a Hind III or Kpn I site. pDHFRIII was digested with Sst II and ligation reactions with either Hind III or Kpn I linkers were done. The resultant plasmids were digested with either Hind III or Kpn I and gel purified. The resultant plasmids were designated either pDHFRIII (Hind III) or pDHFRIII (Kpn I). A 700 bp KpnI-Bgl II fragment (fragment A) was purified from pDHFRIII (Hind III).

The SV40 enhancer sequence was inserted into pDHFRIII (Hind III) by first digesting SV40 DNA with Hind III, and DNA from 5089 to 968 bp was isolated and purified. Plasmid pDHFRIII (Hind III) was phosphatased, and the SV40 DNA and linearized plasmid pDHFRIII (Hind III) were used in a ligation reaction. A 700 bp Eco RI-Kpn I fragment (fragment B) was isolated from the resulting plasmid.

For the final construction of pD3, fragments A (50 ng), B (50 ng) and C (10 ng) were combined in a ligation reaction and used to transform *E. coli* RRI. Positive colonies were isolated and plasmid DNA was prepared.

Plasmid pD3 was modified to accept the insertion of the protein C sequence by converting the Bcl I insertion site to an Eco RI site. First, the Eco RI site present in pD3 (the leftmost terminus in adenovirus 5 0-1) was converted to a Bam HI site via conventional linkering procedures. The resultant plasmid was transformed in *E. coli* HB101. Plasmid DNA was prepared, and positive clones were identified by restriction analysis.

pD3' is a vector identical to pD3 except that the SV40 polyadenylation signal (i.e., the SV40 Bam HI (2533 bp) to Bcl I (2770 bp) fragment) is in the late orientation. Thus, pD3' contains a Bam HI site as the site of gene insertion.

To generate pDX, the Eco RI site in pD3' was converted to a Bcl I site by Eco RI cleavage, incubation with SI nuclease and subsequent ligation with Bcl I linkers. DNA was prepared from a positively identified colony, and a 1.9 kb Xho I-Pst I fragment containing the altered restriction site was prepared via gel purification. In a second modification, Bcl I-cleaved pD3 was ligated with Eco RI-Bcl I adapters in order to generate an Eco RI site as the position for inserting a gene into the expression vector. Positive colonies were identified by restriction analysis. The resulting plasmid, designated pDX, has a unique Eco RI site for insertion of foreign genes The protein C cDNA was inserted into pDX as an Eco RI fragment. Plasmids were screened by restriction analysis. A plasmid having the protein C insert in the correct orientation with respect to the promoter elements and plasmid DNA was designated pDX/PC. Because the cDNA insert in pDX/PC contains a ATG codon in the 5' non-coding region, deletion mutagenesis was performed on the cDNA. Deletion of the three base pairs was performed according to standard procedures or oligonucleotide-directed mutagenesis. The pDX-based vector containing the modified cDNA was designated p594.

C. Modification of the Protein C Processing Site

To enhance the processing of single-chain protein C to the two-chain form, two additional arginine residues were introduced immediately upstream of the $Lys_{156}$-$Arg_{157}$ cleavage site of the precursor protein, resulting in a cleavage site consisting of four basic amino acids, Arg-Arg-Lys-Arg (SEQ ID NO: 20). The resultant mutant precursor of protein C was designated PC962. It contains the sequence Ser-His-Leu-Arg-Arg-Lys-Arg-Asp (SEQ ID NO: 22) at the cleavage site. Processing at the Arg-Asp bond results in a two-chain protein C molecule.

The mutant molecule was generated by altering the cloned cDNA by site-specific mutagenesis (essentially as described by Zoller and Smith, *DNA* 3:479–488, 1984, for the two-primer method) using the mutagenic oligonucleotide ZC962 ($^{5'}$AGTCACCTGAGAAGAAAACGAGACA$^{3'}$; SEQ ID NO: 11). Plasmid p594 was digested with Sst I, and the approximately 87 bp fragment was cloned into M13mp11 and single-stranded template DNA was isolated. Following mutagenesis, a correct clone was identified by sequencing. Replicative form DNA was isolated, digested with Sst I, and the protein C fragment was inserted into Sst I-cut p594. Clones having the Sst I fragment inserted in the desired orientation were identified by restriction enzyme mapping. The resulting expression vector was designated pDX/PC962.

D. Intronless Protein C Construct

To facilitate the cloning of the protein C cDNA, PC962, into pMAD, the cDNA contained in pDX/PC962 was modified to incorporate Eco RV sites at the extremities of the protein C cDNA insert. A 769 bp Sst II-Pst I fragment encompassing the 3' end of PC962 was cloned between the Sst II and Pst I sites of pBluescript II SK® (Stratagene, La Jolla, Calif.). The fragment was excised with Sst II and Eco RV and purified. The 5' portion of PC962 was modified by PCR. The sense oligonucleotide primer for this reaction covered the 5' ATG region of the cDNA and provided an Eco RV site upstream of this in the product. The antisense oligonucleotide primer covered the Sst II site used to generate the Sst II-Eco RV fragment. The resulting PCR product was digested with Eco RV and Sst II and ligated with the Sst II-Eco RV 3' fragment and Eco RV digested pMAD. The resulting plasmid, designated pCORP9 effectively contained the PC962 cDNA flanked by Eco RV sites in an intronless fusion driven by the beta-lactoglobulin promoter.

E. Genomic Protein C DNA Construction

A genomic DNA construct containing exons I through VIII was made. See, U.S. Pat. No. 4,959,318, which is incorporated herein by reference, for disclosure of the exon structure of the protein C gene. This genomic construct, designated GPC10-1, changed the sequence 16 base pairs upstream of the ATG from the native protein C sequence to the beta-lactoglobulin sequence and introduced mutations in the propeptide cleavage site located in exon 2, and the two-chain cleavage site located in exon 6, as described below.

The construct was assembled using four fragments designated A, B, C and D and encompassed the protein C gene sequence from the ATG to a Bam HI site in exon VIII, immediately upstream of the stop codon. The fragments were generated from a human genomic library in λ Charon 4A phage that was screened with a radiolabeled cDNA probe for human protein C. The screening of the λ library produced three clones that together mapped the entire protein C gene (Foster et al., 1985, ibid.). These clones were designated PCλ1, PCλ6 and PCλ8.

Fragment A was a Not I to Eco RI fragment that contained exons I and II of the genomic sequence and was 1698 bp. A subclone of PCλ6 contained an Eco RI to Eco RI fragment and was designated pHCR4.4-1. Using pHCR4.4-1 as a template and oligonucleotides ZC6303 (SEQ ID NO: 12) and ZC6337 (SEQ ID NO: 13), a DNA fragment was generated by polymerase chain reaction (PCR). Oligonucleotide ZC6303 changed the sequence 16 base pairs 5' to the ATG sequence from the native protein C sequence to the equivalent sequence from the beta-lactoglobulin gene and introduced a Not I site. Oligonucleotide ZC6337 changed the propeptide cleavage site from Arg-Ile-Arg-Lys-Arg (SEQ ID NO: 24) to Gln-Arg-Arg-Lys-Arg (SEQ ID NO: 25). The resulting PCR-generated fragment was digested with Not I and Bss HII, and a 1402 base pair fragment was gel purified and designated A1. A second fragment was prepared using a λ gt11 clone of PCλ1 as a template with oligonucleotides ZC6306 (SEQ ID NO: 14) and ZC6338 (SEQ ID NO: 15) in a polymerase chain reaction. The resulting DNA fragment, designated A3, was digested with Bss HII and Eco RI and gel purified, resulting in a 296 base pair fragment. Fragments A1 and A3 were ligated into the Bluescript II KS® phagemid vector (Stratagene, La Jolla, Calif.). The resulting plasmid, designated GPC 2-2, was digested with Not I and Eco RI, gel purified and the Not I-Eco RI DNA fragment was designated Fragment A.

pCR 2-14 is a subclone that contains an Eco RI to Eco RI DNA fragment of PCλ8 (Foster et al., 1985, ibid.). The plasmid was digested with Eco RI and Sst I and gel purified. The resulting fragment was designated Fragment B.

Plasmid pCR 2-14 was used as template DNA with oligonucleotides ZC6373 (SEQ ID NO: 16) and ZC6305 (SEQ ID NO: 17), which introduced an Afl II site and the RRKR mutation of the native (KR) two-chain cleavage site, in a polymerase chain reaction. The resulting PCR-generated fragment was digested with Bgl II and Afl II and gel purified, resulting in a 1441 base pair fragment, designated E1. Fragment E1 was used in a ligation reaction with oligonucleotides ZC6302 (SEQ ID NO: 18) and ZC6304 (SEQ ID NO: 19). These oligonucleotides form Afl II and Sst II restriction sites when annealed and were ligated to the 3' end of fragment E1, resulting in a fragment with a 5' Bgl II site and a 3' Sst II site. This fragment was used in a ligation reaction with a Bam HI-Sst II digested Bluescript II KS® phagemid vector (Stratagene). The resulting plasmid was designated GPC 8-5 and digested with Sst I and Sst II, generating a 626 base pair fragment, designated Fragment C.

A fourth fragment was generated by digestion of a genomic subclone (pHCB7-1) of PCλ8. pHCB7-1 contained a Bgl II to Bgl II fragment that encompassed exons VI through VIII. pHCB7-1 was digested with Sst II and Bam HI and a 2702 base pair fragment was gel purified. The fragment was designated Fragment D.

A five-part ligation reaction was prepared using Not I and Bam HI digested and linearized Bluescript II KS® phagemid vector (Stratagene) with Fragment A (5' Not I to 3' Eco RI) that contained exons I and II, Fragment B (5' Eco RI to 3' Sst I) that contained exons III, IV and V, Fragment C (5' Sst I to 3' Sst II) that contained the 5' portion of exon VI and Fragment D (5' Sst II to 3' Bam HI) that contained the remaining 3' portion of exon VI and exons VII and VIII. The resulting DNA was 8950 base pairs and designated GPC 10-1.

GPC10-1 was originally generated with BLG sequences and a Not I site upstream of the ATG initiator codon and modifications to both cleavage sites. A clone, designated pPC12/BS, was generated to ensure that the 5' Not I site of GPC10-1 would not introduce secondary structure into mRNA molecules that could hinder translation. pPC12/BS was generated using PCR amplification of a 1 kb Not I-Sca I fragment that covered the 5' region of the protein C gene and contained the wild-type ATG codon environment. This introduced an Eco RV site immediately downstream of the Not I site, adjacent to the ATG codon, and a Bam HI site was incorporated 3' of the Sca I site to facilitate cloning. Following a Not I/Bam HI digestion, the PCR product was cloned into Not I-Bam HI digested Bluescript II KS® phagemid vector (Stratagene). The Not I-Eco RV-Sca I fragment present in pPC12/BS was excised, purified and ligated to GPC10-1, which had been linearized with Not I and partially digested with Sca I (the pUC ampillicin gene has an internal Sca I site). The resulting clone was designated GPC10-2 and possesses an Eco RV site immediately upstream of the ATG initiator codon.

GPC10-1 and GPC10-2 both terminated at the final Bam HI site in exon VIII of the protein C gene. To reconstitute the 56 bp of sequence, ending at the termination codon, two oligonucleotides were synthesized with flanking Bam HI (5') and Bgl II (3') restriction sites. Following annealing of the oligonucleotides, the product was cloned into Bam HI digested pBST+ to generate plasmid pPC3'. pBST+ is a derivative of pBS (Stratagene) with a new polylinker. The addition of the polylinker added Bgl II, Xho I, Nar I and Cla I restriction sites from the vector polylinker downstream of the destroyed Bgl II site of the oligonucleotide construct.

The Not I-Bam HI fragment of GPC10-1 was subcloned into Not I/Bam HI digested pPC3' to add 3' coding sequences of protein C, the TAG termination codon followed by Bgl II-Xho I-Nar I-Cla I. The 3' region of the protein C gene beginning with the Eco RV site in intron V was excised from this plasmid on an Eco RV-Cla I fragment.

The Eco RV-Eco RV fragment from GPC10-2, covering the 5' portion of the protein C gene, and the above Eco RI-Cla I fragment covering the 3' portion of the protein C gene were combined between the Eco RV and Cla I sites of pMAD6 (SEQ ID NO: 23) to generate pCORP13. This effectively placed a genomic portion of the protein C gene with modified propeptide and two-chain cleavage sites under the control of the beta-lactoglobulin promoter.

A further genomic construct was generated from pCORP13 that contained only the modified two-chain cleavage site. This was achieved using PCR amplification to modify two fragments which resulting in restoration of the coding capability of exon 2 from the mutant Gln-Arg-Arg-Lys-Arg (SEQ ID NO: 25) to the wild-type Arg-Ile-Arg-Lys-Arg (SEQ ID NO: 24). pCORP13 was used as template for these reactions. The first fragment was 1.3 kb, which encompassed the 5' end of the protein C gene up to the Bam HI site in exon 2. For this reason, the sense primer was designed to add a Hind III site 5' to the Eco RV site proximal to the ATG initiation codon. The antisense primer was designed to restore the wild-type sequences in exon 2, which included a restored Bam HI site. A second fragment of 0.2 kb from the Bam HI site in exon 2 to the Xho I site in intron 2, was also amplified. The two fragments were combined in pGEMII (Promega, Madison, Wis.) to generate pGEMPC1.5. A 7.5 kb Xho I fragment from pCORP 13 was ligated to Xho I digested pGEMPC1.5 to generate a complete protein C genomic sequence covering exons 1–8 with a wild-type propeptide cleavage site and a modified two-chain cleavage site. The plasmid was designated pGEMPC14. The sequence was excised from pGEMPC14 as a Hind III/Sal I fragment. The DNA termini were repaired using a Klenow reaction and the fragment was blunt-end ligated into Eco RV digested pMAD6 (SEQ ID NO: 23) to generate pCORP14.

Example 3

Mice for initial breeding stocks (C57BL6J, CBACA) were obtained from Harlan Olac Ltd. (Bicester, UK). These were mated in pairs to produce F1 hybrid cross (B6CBAF1) for recipient females, superovulated females, stud males and vasectomized males. All animals were kept on a 14 hour light/10 hour dark cycle and fed water and food (Special Diet Services RM3, Edinburgh, Scotland) ad libitum.

Transgenic mice were generated essentially as described in Hogan et al., *Manipulating the Mouse Embryo: A Laboratory Manual*, Cold Spring Harbor Laboratory, 1986, which is incorporated herein by reference in its entirety. Female B6CBAF1 animals were superovulated at 4–5 weeks of age by an i.p. injection of pregnant mares' serum gonadotrophin (FOLLIGON, Vet-Drug, Falkirk, Scotland) (5 iu) followed by an i.p. injection of human chorionic gonadotrophin (CHORULON, Vet-Drug, Falkirk, Scotland) (5 iu) 45 hours later. They were then mated with a stud male overnight. Such females were next examined for copulation plugs. Those that had mated were sacrificed, and their eggs were collected for microinjection.

DNA was injected into the fertilized eggs as described in Hogan et al. (ibid.). Briefly, the vector containing the protein C expression unit was digested with Mlu I, and the expression unit was isolated by sucrose gradient centrifugation. All chemicals used were reagent grade (Sigma Chemical Co., St. Louis, Mo., U.S.A.), and all solutions were sterile and nuclease-free. Solutions of 20% and 40% sucrose in 1 M NaCl, 20 mM Tris pH 8.0, 5 mM EDTA were prepared using UHP water and filter sterilized. A 30% sucrose solution was prepared by mixing equal volumes of the 20% and 40% solutions. A gradient was prepared by layering 0.5 ml steps of the 40%, 30% and 20% sucrose solutions into a 2 ml polyallomer tube and allowed to stand for one hour. 100 $\mu$l of DNA solution (max. 8 $\mu$g DNA) was loaded onto the top of the gradient, and the gradient was centrifuged for 17–20 hours at 26,000 rpm, 15° C. in a Beckman TL100 ultracentrifuge using a TLS-55 rotor (Beckman Instruments, Fullerton, Calif., USA). Gradients were fractionated by puncturing the tube bottom with a 20 ga. needle and collecting drops in a 96 well microtiter plate. 3 $\mu$l aliquots were analyzed on a 1% agarose mini-gel. Fractions containing the protein C DNA fragment were pooled and ethanol precipitated overnight at −20°C. in 0.3M sodium acetate. DNA pellets were resuspended in 50–100 $\mu$l UHP water and quantitated by fluorimetry. The protein C expression unit was diluted in Dulbecco's phosphate buffered saline without calcium and magnesium (containing, per liter, 0.2 g KCl, 0.2 g $KH_2PO_4$, 8.0 g NaCl, 1.15 g $Na_2HPO_4$) or in TE (10 mM Tris-HCl, 1 mM EDTA pH 7.5). DNA concentration is adjusted to about 6 $\mu$g/ml, prior to injection into the eggs (~2 pl total DNA solution per egg).

Recipient females of 6–8 weeks of age are prepared by mating B6CBAF1 females in natural estrus with vasectomized males. Females possessing copulation plugs are then kept for transfer of microinjected eggs.

Following birth of potential transgenic animals, tail biopsies are taken, under anesthesia, at four weeks of age. Tissue samples are placed in 2 ml of tail buffer (0.3 M Na acetate, 50 mM NaCl, 1.5 mM MgCl2, 10 mM Tris-HCl, pH 8.5, 0.5% NP40, 0.5% Tween 20) containing 200 lg/ml proteinase K (Boehringer Mannheim, Mannheim, Germany) and vortexed. The samples are shaken (250 rpm) at 55°–60° C. for 3 hours to overnight. DNA prepared from biopsy samples is examined for the presence of the injected constructs by PCR and Southern blotting. The digested tissue is vigorously vortexed, and 5 ll aliquots are placed in 0.5 ml microcentrifuge tubes. Positive and negative tail samples are included as controls. Forty ll of silicone oil (BDH, Poole, UK) is added to each tube, and the tubes are briefly centrifuged. The tubes are incubated in the heating block of a thermal cycler (e.g. Omni-gene, Hybaid, Teddington, UK) to 95° C. for 10 minutes. Following this, each tube has a 45 $\mu$l aliquot of PCR mix added such that the final composition of each reaction mix is: 50 mM KCl; 2 mM $MgCl_2$; 10 mM Tris-HCl (pH 8.3); 0.01% gelatin; 0.1% NP40, 10% DMSO; 500 nM each primer, 200 $\mu$M dNTPs; 0.02 U/$\mu$l Taq polymerase (Boehringer Mannheim, Mannheim, Germany). The tubes are then cycled through 30 repeated temperature changes as required by the particular primers used. The primers may be varied but in all cases must target the BLG promoter region. This is specific for the injected DNA fragments because the mouse does not have a BLG gene. Twelve $\mu$l of 5× loading buffer containing Orange G marker dye (0.25% Orange G (Sigma) 15% Ficoll type 400 (Pharmacia Biosystems Ltd., Milton Keynes, UK)) is then added to each tube, and the reaction mixtures are electrophoresed on a 1.6% agarose gel containing ethidium bromide (Sigma) until the marker dye has migrated ⅔ of the length of the gel. The gel is visualized with a UV light source emitting a wavelength of 254 nm. Transgenic mice having one or more of the injected DNA fragments are identified by this approach.

Positive tail samples are processed to obtain pure DNA. The DNA samples are screened by Southern blotting using a BLG promoter probe (nucleotides 2523–4253 of SEQ ID NO: 7).

Southern blot analysis of transgenic mice prepared essentially as described above demonstrated that approximately 10% of progeny contained protein C sequences. Examination of milk from positive animals by reducing SDS polyacrylamide gel electrophoresis demonstrated the presence of protein C at concentrations up to 1 mg/ml.

Example 4

Donor ewes are treated with an intravaginal progesterone-impregnated sponge (CHRONOGEST Goat Sponge, Intervet, Cambridge, UK) on day 0. Sponges are left in situ for ten or twelve days.

Superovulation is induced by treatment of donor ewes with a total of one unit of ovine follicle stimulating hormone (OFSH) (OVAGEN, Horizon Animal Reproduction Technology Pty. Ltd., New Zealand) administered in eight intramuscular injections of 0.125 units per injection starting at 5:00 pm on day −4 and ending at 8:00 am on day 0. Donors are injected intramuscularly with 0.5 ml of a luteolytic agent (ESTRUMATE, Vet-Drug) on day −4 to cause regression of the corpus luteum, to allow return to estrus and ovulation. To synchronize ovulation, the donor animals are injected intramuscularly with 2 ml of a synthetic releasing hormone analog (RECEPTAL, Vet-Drug) at 5:00 pm on day 0.

Donors are starved of food and water for at least 12 hours before artificial insemination (A.I.). The animals are artificially inseminated by intrauterine laparoscopy under sedation and local anesthesia on day 1. Either xylazine (ROMPUN, Vet-Drug) at a dose rate of 0.05–0.1 ml per 10 kg bodyweight or ACP injection 10 mg/ml (Vet-Drug) at a dose rate of 0.1 ml per 10 kg bodyweight is injected intramuscularly approximately fifteen minutes before A.I. to provide sedation. A.I. is carried out using freshly collected semen from a Poll Dorset ram. Semen is diluted with equal parts of filtered phosphate buffered saline, and 0.2 ml of the diluted semen is injected per uterine horn. Immediately pre- or post-A.I., donors are given an intramuscular injection of AMOXYPEN (Vet-Drug).

Fertilized eggs are recovered on day 2 following starvation of donors of food and water from 5:00 pm on day 1. Recovery is carried out under general anesthesia induced by an intravenous injection of 5% thiopentone sodium (INTRAVAL SODIUM, Vet-Drug) at a dose rate of 3 ml per 10 kg bodyweight. Anesthesia is maintained by inhalation of 1–2% Halothane/$O_2$/$N_2O$. To recover the fertilized eggs, a laparotomy incision is made, and the uterus is exteriorized. The eggs are recovered by retrograde flushing of the oviducts with Ovum Culture Medium (Advanced Protein Products, Brierly Hill, West Midlands, UK) supplemented with bovine serum albumin of New Zealand origin. After flushing, the uterus is returned to the abdomen, and the incision is closed. Donors are allowed to recover post-operatively or are euthanized. Donors that are allowed to recover are given an intramuscular injection of Amoxypen L.A. at the manufacturer's recommended dose rate immediately pre- or post-operatively.

Plasmids containing the protein C DNA are digested with Mlu I, and the expression unit fragments are recovered and purified on sucrose density gradients. The fragment concentrations are determined by fluorimetry and diluted in Dulbecco's phosphate buffered saline without calcium and magnesium or TE as described above. The concentration is adjusted to 6 μg/ml, and approximately 2 pl of the mixture is microinjected into one pronucleus of each fertilized eggs with visible pronuclei.

All fertilized eggs surviving pronuclear microinjection are cultured in vitro at 38.5° C. in an atmosphere of 5% $CO_2$:5% $O2$:90% $N_2$ and about _100% humidity in a bicarbonate buffered synthetic oviduct medium (see Table) supplemented with 20% v/v vasectomized ram serum. The serum may be heat inactivated at 56° C. for 30 minutes and stored frozen at −20° C. prior to use. The fertilized eggs are cultured for a suitable period of time to allow early embryo mortality (caused by the manipulation techniques) to occur. These dead or arrested embryos are discarded. Embryos having developed to 5 or 6 cell divisions are transferred to synchronized recipient ewes.

TABLE

Synthetic Oviduct Medium

| Stock A (Lasts 3 Months) | |
| --- | --- |
| NaCl | 6.29g |
| KCl | 0.534g |
| $KH_2PO_4$ | 0.162g |
| $MgSO_4.7H_2O$ | 0.182g |
| Penicillin | 0.06g |
| Sodium Lactate 60% syrup | 0.6mls |
| Super $H_2O$ | 99.4mls |
| Stock B (Lasts 2 weeks) | |
| $NaHCO_3$ | 0.21g |
| Phenol red | 0.001g |
| Super $H_2O$ | 10mls |
| Stock C (Lasts 2 weeks) | |
| Sodium Pyruvate | 0.051g |
| Super $H_2O$ | 10mls |
| Stock D (Lasts 3 months) | |
| $CaCl2.2H_2O$ | 0.262g |
| Super $H_2O$ | 10mls |
| Stock E (Lasts 3 months) | |
| Hepes | 0.651g |
| Phenol red | 0.001g |
| Super $H_2O$ | 10mls |
| To make up 10 mls of Bicarbonate Buffered Medium | |
| STOCK A | 1ml |
| STOCK B | 1ml |
| STOCK C | 0.07ml |
| STOCK D | 0.1ml |
| Super $H_2O$ | 7.83ml |
| To make up 10 mls of HEPES Buffered Medium | |
| STOCK A | 1ml |
| STOCK B | 0.2ml |
| STOCK C | 0.07ml |
| STOCK D | 0.1ml |
| STOCK E | 0.8ml |
| Super H2O | 7.83ml |

Osmolarity should be 265–285 mOsm.
Add 2.5 ml of heat inactivated sheep serum and filter sterilize.

Recipient ewes are treated with an intravaginal progesterone-impregnated sponge (Chronogest Ewe Sponge or Chronogest Ewe-Lamb Sponge, Intervet) left in situ for 10 or 12 days. The ewes are injected intramuscularly with 1.5 ml (300 iu) of a follicle stimulating hormone substitute (P.M.S.G., Intervet) and with 0.5 ml of a luteolytic agent (Estrumate, Coopers Pitman-Moore) at sponge removal on day −1. The ewes are tested for estrus with a vasectomized ram between 8:00 am and 5:00 pm on days 0 and 1.

Embryos surviving in vitro culture are returned to recipients (starved from 5:00 pm on day 5 or 6) on day 6 or 7. Embryo transfer is carried out under general anesthesia as described above. The uterus is exteriorized via a laparotomy incision with or without laparoscopy. Embryos are returned to one or both uterine horns only in ewes with at least one suitable corpora lutea. After replacement of the uterus, the abdomen is closed, and the recipients are allowed to recover. The animals are given an intramuscular injection of Amoxypen L.A. at the manufacturer's recommended dose rate immediately pre- or post-operatively.

Lambs are identified by ear tags and left with their dams for rearing. Ewes and lambs are either housed and fed complete diet concentrates and other supplements and or ad lib. hay, or are let out to grass.

Within the first week of life (or as soon thereafter as possible without prejudicing health), each lamb is tested for the presence of the heterologous DNA by two sampling procedures. Following tail biopsy, within a week, a 10 ml blood sample is taken from the jugular vein into an EDTA vacutainer. Tissue samples are taken by tail biopsy as soon as possible after the tail has become desensitized after the application of a rubber elastrator ring to its proximal third (usually within 200 minutes after "tailing") The tissue is placed immediately in a solution of tail buffer. Tail samples are kept at room temperature and analyzed on the day of collection. All lambs are given an intramuscular injection of Amoxypen L.A at the manufacturer's recommended dose rate immediately post-biopsy, and the cut end of the tail is sprayed with an antibiotic spray.

DNA is extracted from sheep blood by first separating white blood cells. A 10 ml sample of blood is diluted in 20 ml of Hank's buffered saline (HBS; obtained from Sigma Chemical Co.). Ten ml of the diluted blood is layered over 5 ml of Histopaque (Sigma) in each of two 15 ml screw-capped tubes. The tubes are centrifuged at 3000 rpm (2000×g max.), low brake for 15 minutes at room temperature. White cell interfaces are removed to a clean 15 ml tube and diluted to 15 ml in HBS. The diluted cells are spun at 3000 rpm for 10 minutes at room temperature, and the cell pellet is recovered and resuspended in 2–5 ml of tail buffer.

To extract DNA from the white cells, 10% SDS is added to the resuspended cells to a final concentration of 1%, and the tube is inverted to mix the solution. One mg of fresh proteinase K solution is added, and the mixture is incubated overnight at 45° C. DNA is extracted using an equal volume of phenol/chloroform (×3) and chloroform/isoamyl alcohol (×1). The DNA is then precipitated by adding 0.1 volume of 3 M NaOAc and 2 volumes of ethanol, and the tube is inverted to mix. The precipitated DNA is spooled out using a clean glass rod with a sealed end. The spool is washed in 70% ethanol, and the DNA is allowed to partially dry, then is redissolved in TE (10 mM Tris-HCl, 1 mM EDTA, pH 7.5).

DNA samples from blood and tail are analyzed by Southern blotting using probes for the BLG promoter region and the protein C coding regions.

Example 5

A founder female animal, designated 30851, which is transgenic for both BLG and pCORP9 was generated. She has given rise to two sons and a transgenic daughter, designated 40387. Recombinant transgenic protein C was purified from milk (from 30851) by a single chromatography step using a calcium-dependent monoclonal antibody affinity column. Briefly, the milk samples were pooled up to a volume of 40 ml. Two volumes of ice-cold 1×TBS (50 mM Tris-HCl, 150 mM NaCl pH 6.5) and 200 mM EDTA, pH 6.5 were added to solubilise the caseins. The EDTA-treated milk solution was centrifuged at 15,000 rpm for 30 minutes at 4° C. in a JA20 rotor (Beckman Instruments, Irvine, Calif.). After centrifugation, the upper lipid phase and the small pellet were discarded.

The EDTA-treated milk was diluted with an equal volume of ice-cold 1×TBS and 133 mM $CaCl_2$ while stirring. A cloudy precipitate formed upon addition of the $CaCl_2$. The pH was quickly adjusted by addition of a few drops of 4 M NaOH, and the precipitate was redissolved. Any remaining insoluble material was removed by filtration through a 0.45 μm filter.

The optical density of the solubilised milk was measured at 280 nm, and the protein concentration was calculated. The milk was diluted to a protein concentration of 10 mg/ml using 1×TBS containing $CaCl_2$ to give a final $Ca^{++}$ concentration of 25 mM. The milk was used to resuspend antibody-Sepharose that carried the immobilized $Ca^{++}$-dependent monoclonal antibody PCL-2, and had been washed in 1×TBS and 25 mM $CaCl_2$. PCL-2 is a monoclonal antibody that binds single chain and two chain protein C, whether or not they are gamma-carboxylated. The milk-Sepharose mixture was incubated overnight at 4° C.

The matrix was washed twice in batch with 1×TBS and 25 mM $CaCl_2$ and packed into a glass column. The resin was washed at a flow rate of 1 ml/min with a calcium containing buffer and a stable baseline was achieved before the bound protein was eluted with an isocratic elution using 1×TBS and 25 mM EDTA, pH 6.5. Fractions containing protein C were pooled and concentrated to approximately 1 ml using an Amicon ultrafiltration unit with a 10 kDa cut-off membrane (Amicon, Danvers, Mass.).

The monoclonal antibody, PCL-2, was coupled to the activated Sepharose 4B as follows: 1 g (3.5 ml of gel) of cyanogen bromide activated Sepharose 4B (Pharmacia LKB Biotechnology, Piscataway, N.J.) was swollen for 15 minutes in 1 mM HCl. The swollen gel was resuspended in 0.1 M $NaHCO_3$, 0.5 M NaCl pH 8.3 and washed several times. The washed gel was resuspended in 11 ml of monoclonal antibody solution (PCL-2, 3.5 mg/ml in bicarbonate buffer pH 8.3) with a coupling ratio of approximately 10 mg/ml gel. Coupling was allowed to proceed for 2 h at room temperature on a rotary mixer, and the gel was recovered by gentle centrifugation. The monoclonal supernatant was removed and replaced by 1 M ethanolamine in order to block any remaining sites on the Sepharose. Blocking was performed overnight at 4° C. Excess adsorbed protein was removed by sequential acid and alkali washes (0.1 M acetate, 0.5 M NaCl pH 4.0; 0.1 M $NaHCO_3$, 0.5 M NaCl pH 8.3), and the coupled gel was stored in 50 mM Tris-HCl, 150 mM NaCl pH 6.5, 0.02% azide.

Example 6

Samples of purified recombinant transgenic protein C were compared with plasma-derived protein C and a plasma-derived activated protein C (APC) preparations. Samples were run on SDS PAGE 4–20% acrylamide gradient gels under reducing conditions and silver stained for protein.

The plasma-derived material shows the presence of a heavy-chain doublet around 44 kDa (FIG. 1, Lane 1). This has been reported to be due to partial occupancy of the three possible N-linked glycosylation sites on the molecule. A similar doublet, although of a slightly lower mass presumably due to some subtle change in glycosylation profile, has also been seen with the transgenic protein C. The light chain was visible around 22 kDa for both preparations. Significantly, in the case of the plasma-derived material uncleaved single-chain was clearly visible above the heavy chain doublet. Plasma-derived protein normally contained 5–10 percent of this inactive material. In contrast, the transgenic protein C contains no obvious single chain by this gel analysis. Therefore, it contains less than a few percent at most of inactive material. This most likely reflects the increased efficiency of cleavage of the modified inter-chain site. In further support of this observation no single chain was visible by direct western blot analysis of transgenic sheep milk (40387, expression level 300 μg/ml).

The purified transgenic protein C was further characterized as follows:

A. ELISA

An enzyme-linked immunosorbent assay (ELISA) for protein C was done as follows: Affinity-purified polyclonal antibody to human protein C (100 μl of 1 μg/ml in 0.1 M $Na_2CO_3$, pH 9.6) was added to each well of a 96-well microtiter plate, and the plates were incubated overnight at 4° C. The wells were then washed three times with phosphate buffered saline (PBS) containing 0.05% Tween-20 and incubated with 100 μl of 1% bovine serum albumin (BSA), 0.05% Tween-20 in PBS at 4° C. overnight. The plates were then rinsed several times with PBS, air dried and stored at 4° C. To assay samples, 100 μl of each sample was incubated for 1 h at 37° C. with a biotin-conjugated sheep polyclonal antibody to protein C (30 ng/ml) in PBS containing 1% BSA and 0.05% Tween-20. After incubation, the wells were rinsed with PBS, and alkaline phosphatase activity was measured by the addition of 100 μl of phosphatase substrate (Sigma, St. Louis, Mo.) in 10% diethanolamine, pH 9.8, containing 0.3 mM $MgCl_2$. The absorbance at 405 nm was read on a microtiter plate reader. Quantitation was by comparison with a standard curve using plasma-derived protein C quantitated by amino acid analysis.

B. Amino-Terminal Sequencing

Amino-terminal sequencing of the transgenic material was performed to ascertain the extent of prosequence removal and to evaluate the presence of gamma-carboxylation. There were three possible N-terminal sequences of protein C. These were: 1) Prosequence which directs gamma-carboxylation and could have remained on the light chain if the first cleavage site was incompletely processed, 2) the light chain and 3) the heavy chain. N-terminal sequencing of protein C obtained from transgenic milk should have contained only the latter two sequences if correct processing had occurred at both of the cleavage sites. Amino-terminal sequencing would have also been expected to reveal the presence of gamma-carboxylation in the light chain. There are nine sites of carboxylation in the first twenty-nine amino acids of the light chain. On an analysis of released amino acids, the PTH-gamma carboxylic acid derivatives eluted from the HPLC column in the break-through and could therefore be analyzed. Thus, a gamma carboxylic acid showed up on the amino-terminal sequence as a space rather than a glutamic acid.

The yields of amino acids in pmol released from the sequencing of approximately 27 pmol (1.4 μl) of purified transgenic protein C corresponded well to those expected for an equimolar mixture of light and heavy chains, and no obvious sequence was discernible for the prosequence. Moreover, no other aberrant sequences were detected, thus indicating a lack of inappropriate proteolytic cleavages.

Figure 2A:
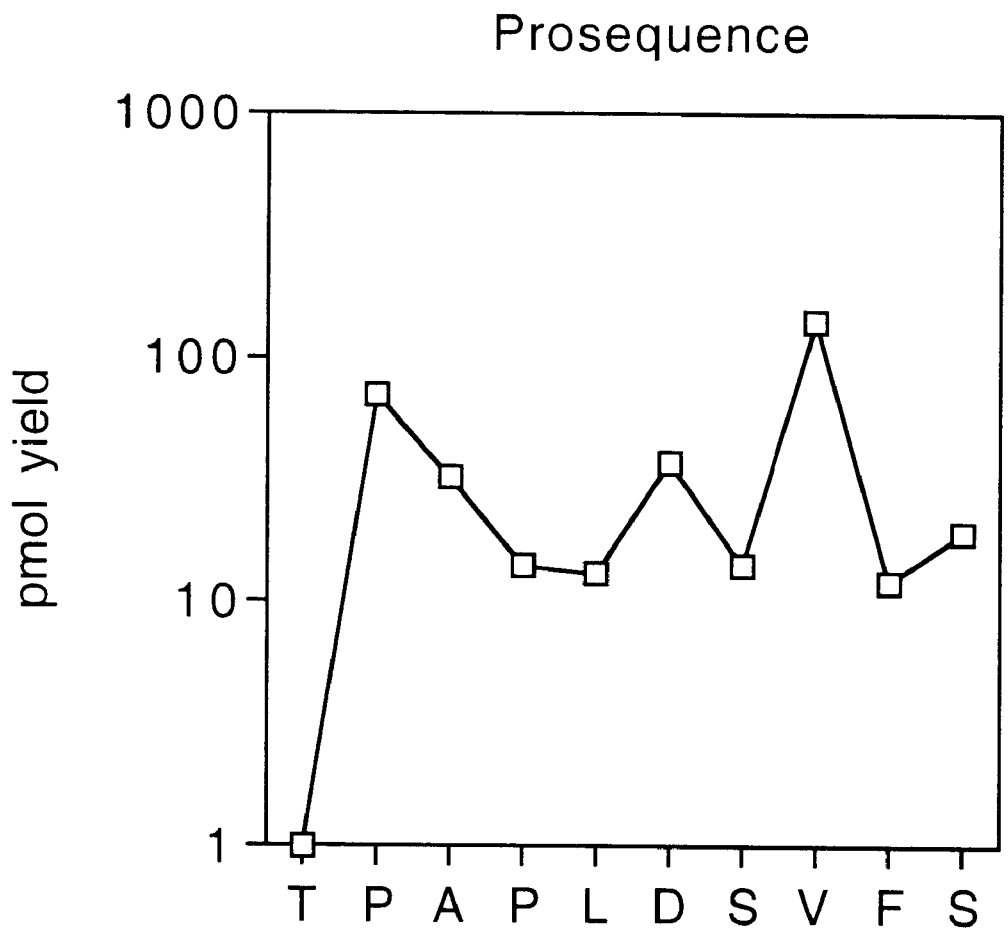
FIG. 2 illustrates sequencing of protein C from sheep line 30851. The initial yields were prosequence=9 pmol, light chain=563 pmol and heavy chain=565 pmol.
Figure 2B:
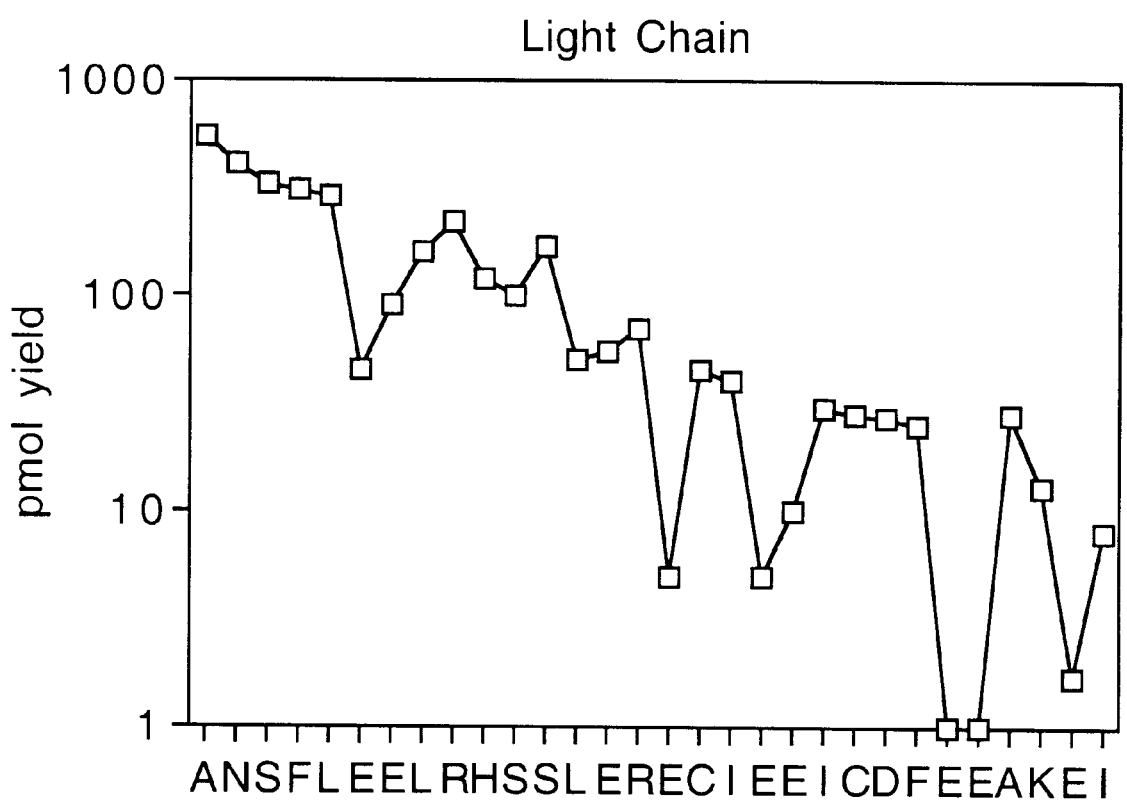
Figure 2C:
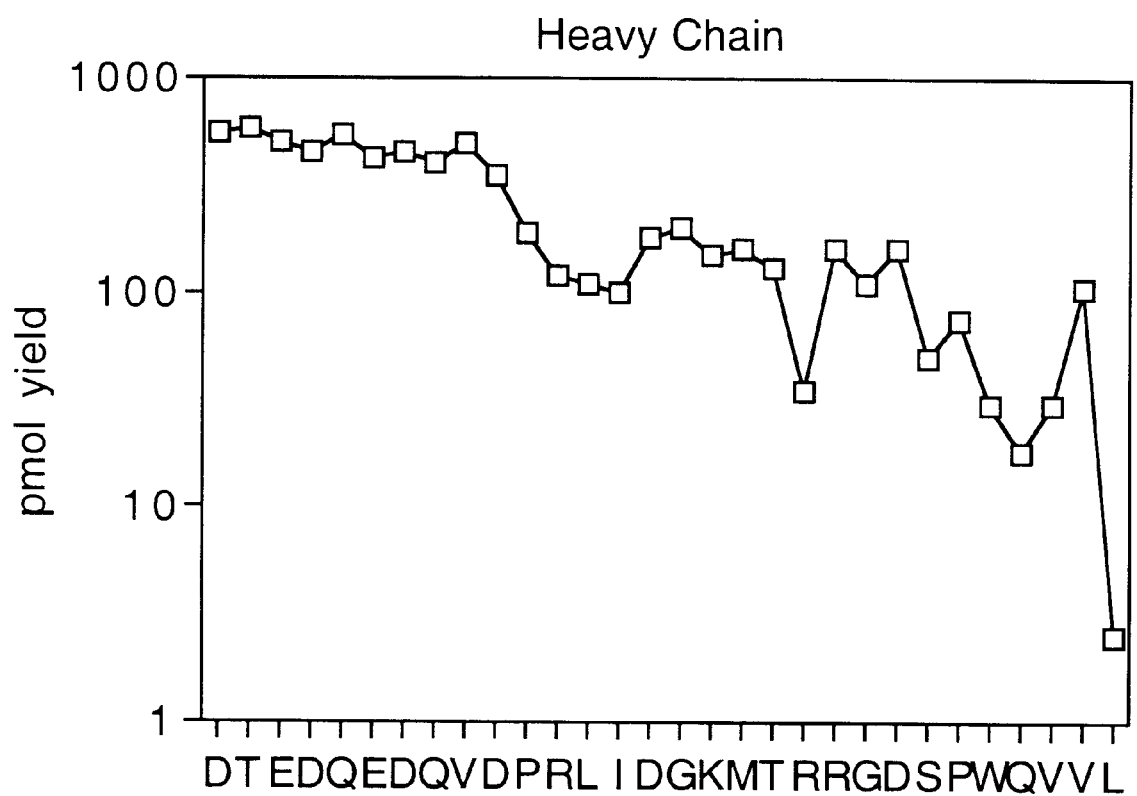

As stated previously, gamma-carboxylated glutamate residues were expected to sequence as blanks using standard instrument conditions. However, sequencing protein C gives a double sequence which must be deconvoluted using knowledge of the expected light and heavy chain sequences. Normally, if the light chain alone were sequenced the gla residues at positions six and seven would appear as blanks. However when sequenced as intact protein C, the heavy chain sequence contains a glutamate residue at position six. Therefore, the only indirect confirmation of the presence of a gla residue in the light chain was the absence of glutamate at position seven which was not 'over written' by a glutamate in the heavy chain (FIG. 2). Two other indirect confirmations of the presence of gamma carboxylation of the transgenic product are described below.

C. Mass Analysis of the Purified Light Chain

The protein sequence of the transgenic-derived protein C precursor had been modified with an Arg-Arg-Lys-Arg (SEQ ID NO: 20) cleavage site between the light and heavy chains to promote more efficient cleavage of the single chain to 2-chain form. Western blot analysis of the transgenic protein C milk and examination of the purified protein C on reducing gels had already confirmed that efficient cleavage had occurred. Normally during secretion, but after cleavage of the plasma-derived material, the two basic amino acids at the carboxy-terminus of the light chain are trimmed back by a basic carboxypeptide. Establishing whether the carboxy-terminus of the transgenic protein C light chain had been processed to remove the two extra basic amino acids introduced by this modification, as well as the two natural ones, was achieved by measuring the mass of the purified light chain in a quadropole instrument using on-line liquid chromatography and electro-spray ionization. In order to achieve this, all of the cysteine residues of protein C were reduced and alkylated, and then the two chains were separated by reversed-phase chromatography.

C1. Reductive Alkylation

Because protein C is heavily cross-linked for a molecule of approximately 52 kDa, with twelve disulfide bridges (17 of the 24 cysteines involved are in the light chain), it was necessary to reductively alkylate the entire protein before attempting to separate the chains by reversed-phase chromatography. In view of the large number of cysteines in the light chain, alkylatation was done with iodoacetamide, in place of the more commonly used vinyl pyridine, to prevent the molecule from becoming excessively hydrophobic.

The transgenic protein C material (6 nmol of protein or 144 pmol of thiol) was reductively alkylated as follows: 0.5 mg of protein C (by ELISA) in 0.5 ml of TBS was added to 50 µl of 1 M Tris pH 8.0, 450 µl water, 570 mg guanidinium chloride, and 10 µl at 50 mg/ml DTT (0.3 µmol representing a 20 fold excess of added thiol over cysteine thiol. The mixture was incubated for 2 hours at 37° C. After incubation, 20 µl at 120 mg/ml iodoacetamide (0.6 M representing a 2 fold excess over DTT on a molar basis) was added, and the mixture was incubated in the dark for one hour at 4° C. The reaction was quenched by adding 50 µl at 50 mg/ml DTT representing a 2.5 fold excess over iodoacetamide. The sample (final volume 1.5 ml) was stored at −20° C. until analysis.

D. Purification of the Light Chain

Purification of protein C light chain was achieved using a large pore polystyrene column with divinyl benzene interactive groups (PLRP-S, 4000Å, 8 µm, 2.1 mm ID: Polymer Laboratories, Shropshire, UK). The optimum conditions for separation of the heavy and light chains were determined to be: solvent A (0.1% TFA) and solvent B (100% acetonitrile) at a flow of 0.5 ml/min with a detector wavelength of 215 nm and a gradient of 30 to 60% solvent B over 60 min.

Fractions were collected across the eluted peaks, and samples (10 µl) were analyzed by SDS PAGE on 4–20% gradient acrylamide gels under non-reducing conditions. The light chain (fractions 3 to 5) was completely resolved from both the heavy chain (fractions 7 to 9) and a single fraction (6) which contained a mixture of heavy chain and what appeared to be unglycosylated light chain.

A sample containing fully resolved light chain was prepared for deglycosylation by centrifugal evaporation under reduced pressure at room temperature. Deglycosylation was carried out using peptide N-glycanase (PNGase; Oxford Glycosystems, Oxford, UK). The protein sample was redissolved in 50 µl of buffer and incubated overnight with 1 unit (5 µl) PNGase, according to manufacturer's specifications.

The light chain was purified from reduced and alkylated plasma-derived protein C by the same method and deglycosylated for further analysis.

E. Analysis by Mass Spectroscopy

Samples of purified light chain were subjected to mass analysis using a liquid chromatography—electrospray interface to a Sciex Quadropole Mass Analyser (Sciex/Perkin Elmer, Toronto, Calif.). The LC system used a 0.5 mm ID column packed with PLRP-S 4000Å, 8 µm resin (Polymer Laboratories). The solvent system contained buffer A (0.1% formic acid), buffer B (0.1% formic acid and a 5:2 (v/v) mixture of ethanol to propan-1-ol). The gradient used was from 5–60% buffer B over 35 minutes at a flow rate of 25 µl per minute. The outflow of the column was linked via a UV detector to the mass spectrometer which was run in positive-ion mode.

The purified and deglycosylated transgenic light chain was analyzed and gave a relatively weak spectrum which was reconstructed to give two components with masses of 18,911.0 and 18,971.0. The plasma light chain was also analyzed and gave a stronger signal with a single major component. The spectrum of the plasma light chain was reconstructed to give a single mass of 18,970.0.

The predicted mass for the light chain carrying nine gamma-carboxy glutamic acids, one β-hydroxy aspartic acid and seventeen carbamidomethyl cysteine residues and ending with $Leu_{155}$ was 18966.9723, which is very close to the masses detected for the transgenic (18,971.0) and plasma-derived (18,970.0) light chains. The small differences in mass were well within the accuracy limitations for this instrument, particularly with the LC delivery. This shows that the mass of the redirectively-alkylated and deglycosylated transgenic light chain is essentially identical to that for the plasma-derived protein C. This implies that both molecules have undergone the same post-translational modifications and that the transgenic material is fully gamma carboxylated, has had all four basic amino acids trimmed back from the carboxy-terminus of the light chain and has single β hydroxy-alanine.

F. Activity Measurements

Figure 3:
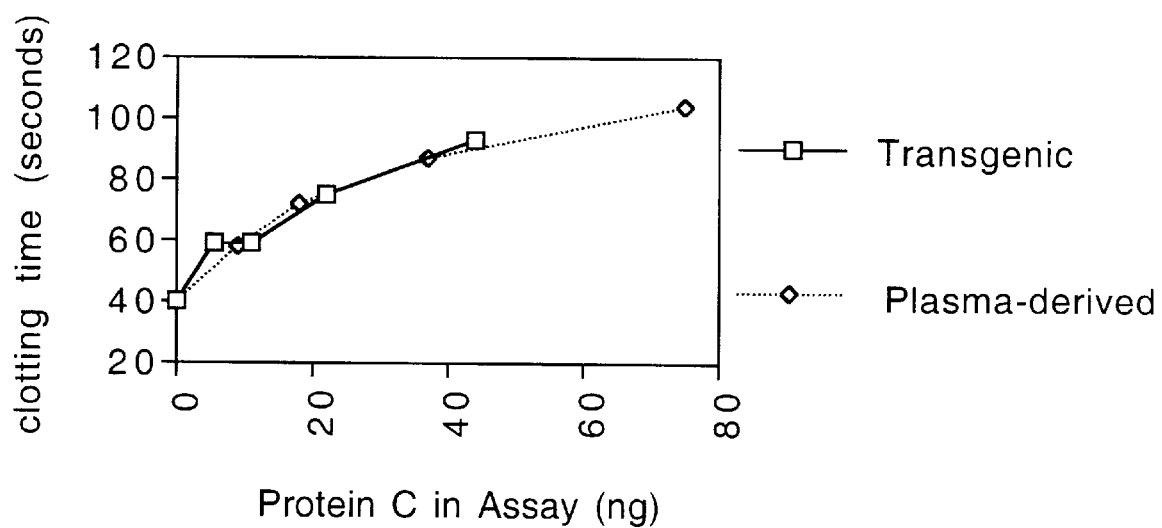
FIG. 3 illustrates clotting activity of transgenic protein C compared to plasma-derived protein C.

The activity of the transgenic protein C was compared with that of the plasma-derived material in a coagulation assay. First each sample of protein C, quantitated by amino acid composition analysis, was activated by incubation with Protac, a snake venom (American Diagnostica Inc, Greenwich, Conn.) at a venom to protein ratio of 1 Unit Protac: 10 µg protein C for 60 minutes at 37° C. Aliquots of the activated material were then compared for their ability to prolong the clotting time of protein C depleted human plasma (Diagnostic Reagents Ltd) in the presence of activated partial thromboplastin time reagent—cephalin from rabbit brain (Sigma) and calcium using a mechanical coagulometer (Diagnostica Stago, Asmieres, FR) A comparison of clotting times with various additions of transgenic and plasma-derived protein C (FIG. 3) shows that the two preparations had the same anti-coagulant activity per mg of protein.

In summary, results show that the sheep-derived transgenic protein C is correctly post-translationally processed, with respect to gamma-carboxylation and probably beta-hydroxylation, and has anticoagulant activity fully equivalent to a high quality purified plasma standard. The results demonstrate that the C-terminal processing of the light chain, with the modified RRKR cleavage site rather than the naturally occurring KR site, has the two extra basic amino acids removed along with the natural ones.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method for producing protein C in a transgenic non-human mammal comprising:

providing a DNA construct comprising a first DNA segment encoding a secretion signal and a protein C propeptide operably linked to a second DNA segment encoding protein C, wherein the encoded protein C comprises a two-chain cleavage site modified from Lysine (Lys)-Arginine (Arg) to $R_1$-$R_2$-$R_3$-$R_4$, and wherein each of $R_1$, $R_2$, $R_3$, $R_4$ is individually Lys or Arg, and wherein said first and second segments are operably linked to additional DNA segments required for expression of the protein C DNA in a mammary gland of a host female non-human mammal;

introducing said DNA construct into a fertilized egg of a non-human mammalian species;

inserting said egg into an oviduct or uterus of a female of said species to obtain offspring carrying said DNA construct;

breeding said offspring to produce female progeny that express said first and second DNA segments and produce milk containing protein C encoded by said second segment, wherein said protein has anticoagulant activity upon activation;

collecting milk from said female progeny; and recovering the protein C from the milk.

2. The method of claim 1, further comprising the step of activating the protein C.

3. The method of claim 1, wherein $R_1$-$R_2$-$R_3$-$R_4$ is Arg-Arg-Lys-Arg (SEQ ID NO: 20).

4. The method of claim 1, wherein said species is selected from sheep, rabbits, cattle and goats.

5. The method of claim 1, wherein each of said first and second DNA segments comprises an intron.

6. The method of claim 1, wherein the second DNA segment comprises a DNA sequence of nucleotides as shown in Seq. ID NO: 1 or Seq. ID. NO: 3.

7. The method of claim 6, wherein the second DNA segment comprises the DNA sequence of nucleotides as shown in SEQ. ID. NO: 1.

8. The method of claim 1, wherein the additional DNA segments comprise a transcriptional promoter selected from the group consisting of casein, β-lactoglobulin, α-lactalbumin and whey acidic protein gene promoters.

9. The method of claim 8, wherein the transcriptional promoter is the β-lactoglobulin gene promoter.

10. A transgenic non-human female mammal whose genome comprises a DNA construct comprising a first EDNA segment encoding a secretion signal and a protein C propeptide operably linked to a second DNA segment encoding protein C, wherein the encoded protein C comprises a two-chain cleavage site modified from Lysine (Lys)-Arginine (Arg) to $R_1$-$R_2$-$R_3$-$R_4$, and wherein each of $R_1$, $R_2$ , $R_3$, $R_4$ is individually Lys or Arg, and wherein said first and second segments are operably linked to additional DNA segments required for the expression of the protein C DNA in the mammary gland of the mammal such that expression of the DNA construct results in the production of recoverable amounts of human protein C in milk of the mammal wherein at least 90% of the human protein C in the milk is two chain protein C.

11. A process for producing a transgenic offspring of a non-human mammal comprising:

providing a DNA construct comprising a first DNA segment encoding a secretion signal and a protein C propeptide operably linked to a second DNA segment encoding protein C, wherein the encoded protein C comprises a two-chain cleavage site modified from Lys-Arg to $R_1$-$R_2$-$R_3$-$R_4$, and wherein each of $R_1$, $R_2$, $R_3$, $R_4$, is individually Lys or Arg, and wherein said first and second segments are operably linked to additional DNA segments required for expression of the protein C DNA in the mammary gland of a host female mammal;

introducing said DNA construct into a fertilized egg of a non-human mammalian species; and inserting said egg into an oviduct or uterus of a female of said species to obtain offspring carrying said DNA construct.

12. The process according to claim 11, wherein $R_1$-$R_2$-$R_3$-$R_4$ is Arg-Arg-Lys-Arg (SEQ ID NO: 20).

13. The process according to claim 11, wherein the offspring is female.

14. The process according to claim 11, wherein the offspring is male.

15. A non-human mammal produced according to the process of claim 11, wherein expression of the DNA construct results in the production of recoverable amounts of human protein C in milk, wherein the protein C has anticoagulant activity upon activation.

16. A non-human mammal of claim 15, wherein the mammal is female.

17. A non-human mammalian embryo whose genome comprises a DNA construct comprising a first DNA segment encoding a secretion signal and a protein C propeptide operably linked to a second DNA segment encoding protein C, wherein the encoded protein C comprises a two-chain cleavage site modified from Lysine (Lys)-Arginine (Arg) to $R_1$-$R_2$-$R_3$-$R_4$, and wherein each of $R_1$, $R_2$, $R_3$, $R_4$ is individually Lys or Arg, and wherein said first and second segments are operably linked to additional DNA segments required for the expression of the protein C DNA in the mammary gland of the mammal such that the embryo develops into a transgenic non-human mammal such that expression of the DNA construct in the transgenic non-human mammal results in the production of recoverable amounts of human protein C in milk of the mammal wherein at least 90% of the human protein C in the milk is two chain protein C.

* * * * *